United States Patent
Andersson et al.

(10) Patent No.: US 11,883,662 B2
(45) Date of Patent: Jan. 30, 2024

(54) IMPLANTABLE MAGNET ARRANGEMENTS

(71) Applicant: Cochlear Limited, Macquarie University (AU)

(72) Inventors: Marcus Andersson, Mölnlycke (SE); Daniel Smyth, Dublin (IE); Fysh Dadd, Lane Cove (AU); Kristien Johanna Maria Verhoeven, Mechelen (BE); Claudiu G. Treaba, New York, NY (US); Jonathon Kirk, New York, NY (US); Charles Roger Aaron Leigh, Epping (AU)

(73) Assignee: Cochlear Limited, Macquarie University (AU)

( * ) Notice: Subject to any disclaimer, the term of this patent is extended or adjusted under 35 U.S.C. 154(b) by 450 days.

(21) Appl. No.: 17/019,634

(22) Filed: Sep. 14, 2020

(65) Prior Publication Data
US 2021/0031037 A1    Feb. 4, 2021

Related U.S. Application Data

(63) Continuation of application No. 15/728,645, filed on Oct. 10, 2017, now Pat. No. 10,792,503, which is a (Continued)

(51) Int. Cl.
*A61N 1/375* (2006.01)
*A61N 1/36* (2006.01)
(Continued)

(52) U.S. Cl.
CPC ..... *A61N 1/36038* (2017.08); *A61N 1/36036* (2017.08); *A61N 1/3758* (2013.01);
(Continued)

(58) Field of Classification Search
CPC ............ A61N 1/36038; A61N 1/36036; A61N 1/37229; A61N 1/37518; A61N 1/3758; A61N 1/0541; A61N 1/375; A61N 1/3787
See application file for complete search history.

(56) References Cited

U.S. PATENT DOCUMENTS

| 6,308,101 B1 | 10/2001 | Faltys et al. |
| 8,133,215 B2 | 3/2012 | Gibson |

(Continued)

FOREIGN PATENT DOCUMENTS

| WO | 03-092326 A1 | 11/2003 |
| WO | 03092326 A1 | 11/2003 |

(Continued)

OTHER PUBLICATIONS

International Search Report and Written Opinion in corresponding International Application No. PCT/IB2016/054921, dated Dec. 2, 2016, 12 pages.

*Primary Examiner* — Eugene T Wu
(74) *Attorney, Agent, or Firm* — Edell, Shapiro & Finnan, LLC

(57) ABSTRACT

Presented herein are magnet arrangements for use with encapsulated implantable components. An implantable component comprises an implant body and a plurality of wire loops forming an internal coil that are encapsulated in a biocompatible overmolding. The implantable component
(Continued)

also comprises a bone fixture positioned proximate to the plurality of wire loops and an implantable magnet attached to the bone fixture.

22 Claims, 18 Drawing Sheets

Related U.S. Application Data continuation of application No. 15/157,631, filed on May 18, 2016, now abandoned.

(60) Provisional application No. 62/206,382, filed on Aug. 18, 2015.

(51) Int. Cl.
  *A61N 1/372* (2006.01)
  *A61N 1/378* (2006.01)
  *A61N 1/05* (2006.01)

(52) U.S. Cl.
  CPC ..... *A61N 1/37229* (2013.01); *A61N 1/37518* (2017.08); *A61N 1/0541* (2013.01); *A61N 1/375* (2013.01); *A61N 1/3787* (2013.01); *H04R 2225/67* (2013.01)

(56) References Cited

U.S. PATENT DOCUMENTS

| | | |
|---|---|---|
| 8,255,058 B2 | 8/2012 | Gibson et al. |
| 9,031,662 B2 | 5/2015 | Leigh et al. |
| 9,144,676 B2 | 9/2015 | Gibson et al. |
| 2005/0004629 A1 | 1/2005 | Gibson et al. |
| 2006/0204717 A1 | 9/2006 | Deininger et al. |
| 2008/0221641 A1* | 9/2008 | Hochmair ............... A61F 11/04 607/57 |
| 2009/0287278 A1 | 11/2009 | Charvin |
| 2011/0137391 A1 | 6/2011 | Leigh |
| 2012/0022647 A1 | 1/2012 | Leigh et al. |
| 2013/0035540 A1 | 2/2013 | Ball |
| 2015/0087892 A1* | 3/2015 | Tourrel ............... A61N 1/37518 607/57 |
| 2015/0367126 A1 | 12/2015 | Smyth |
| 2016/0361537 A1 | 12/2016 | Leigh et al. |

FOREIGN PATENT DOCUMENTS

| | | | |
|---|---|---|---|
| WO | 2014-164023 A1 | 10/2014 | |
| WO | 2017027045 A1 | 2/2017 | |
| WO | WO-2017027045 A1 * | 2/2017 | ......... A61N 1/36036 |

* cited by examiner

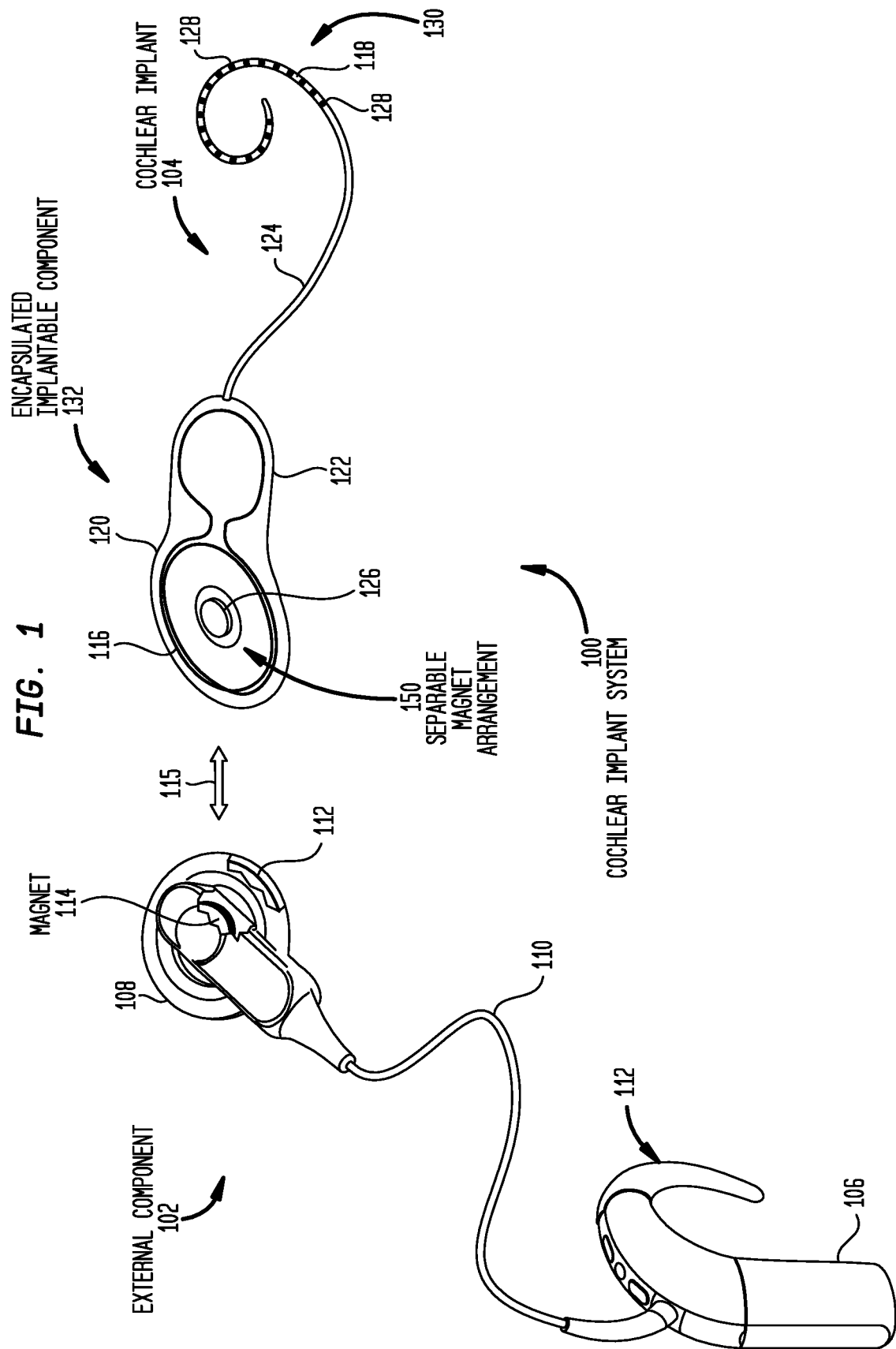

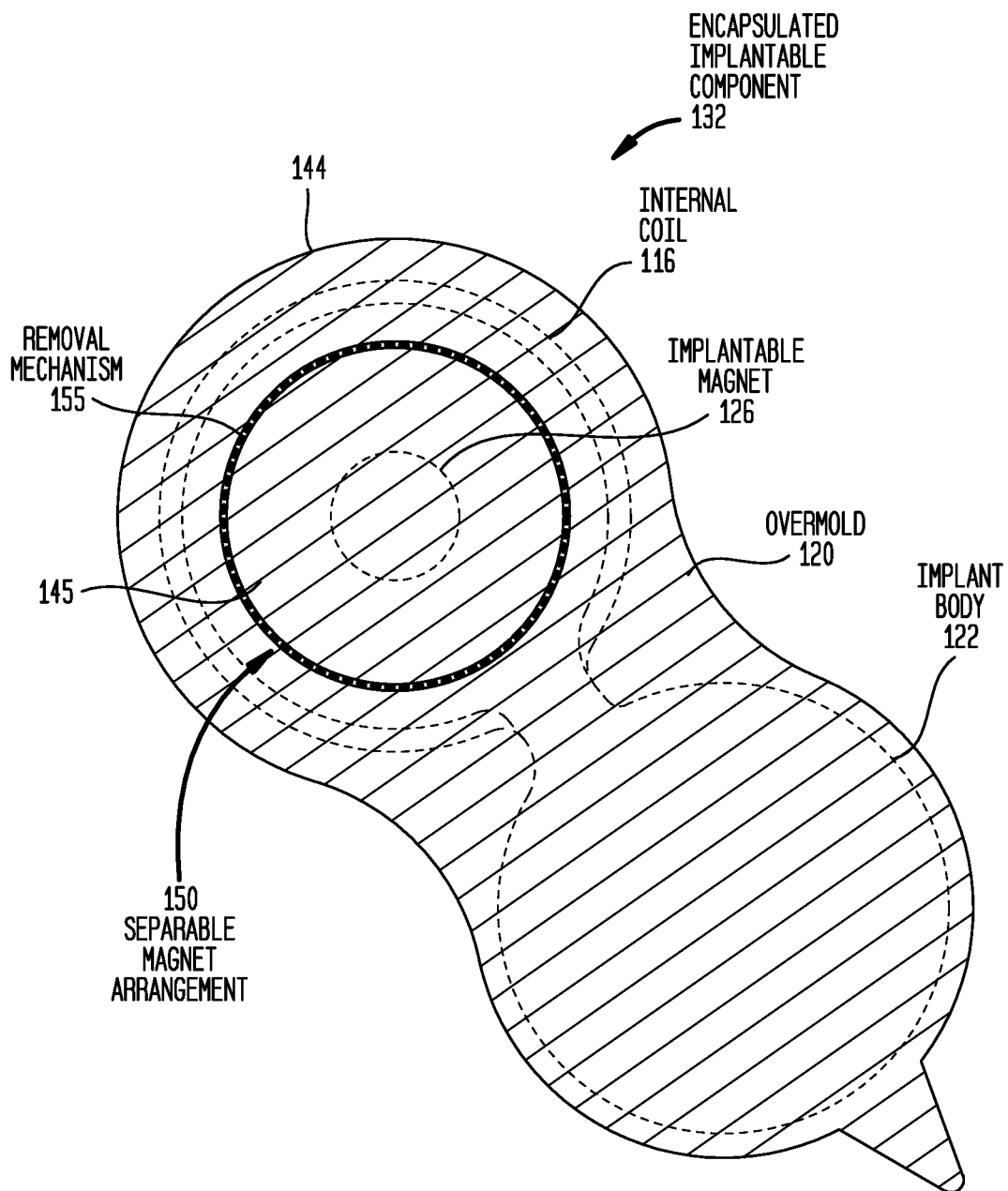

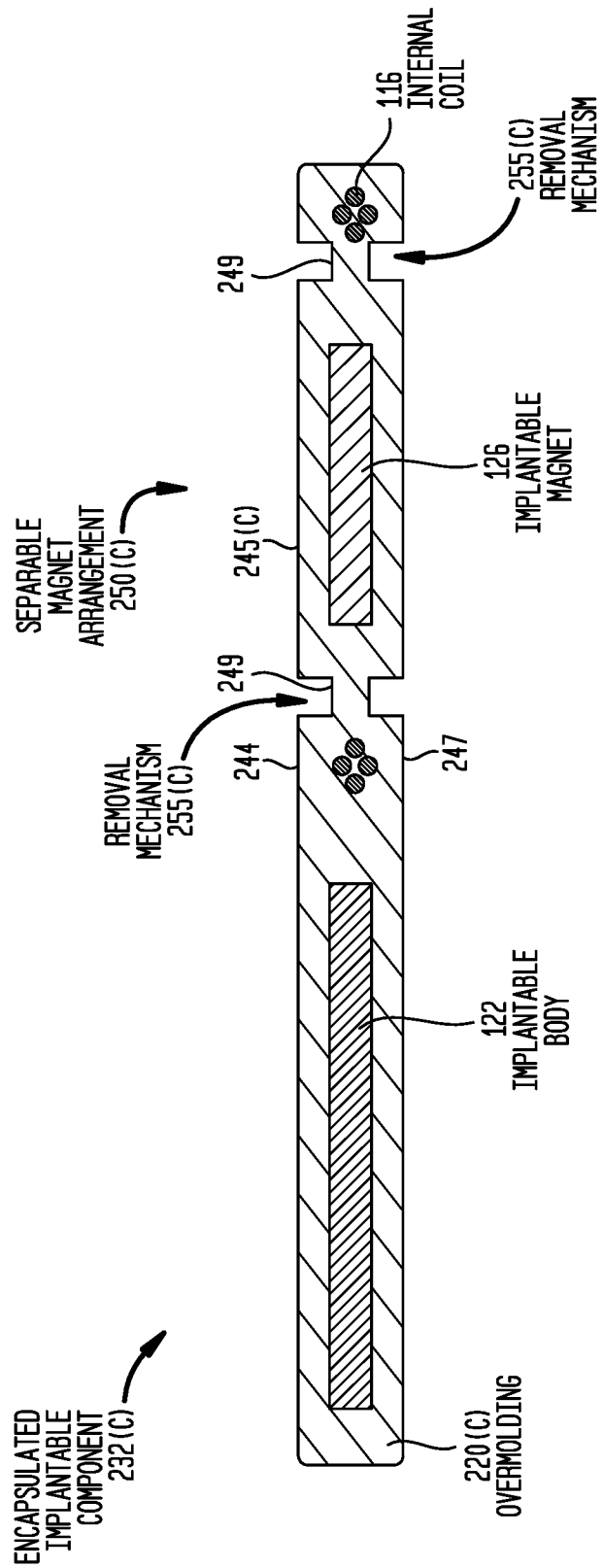

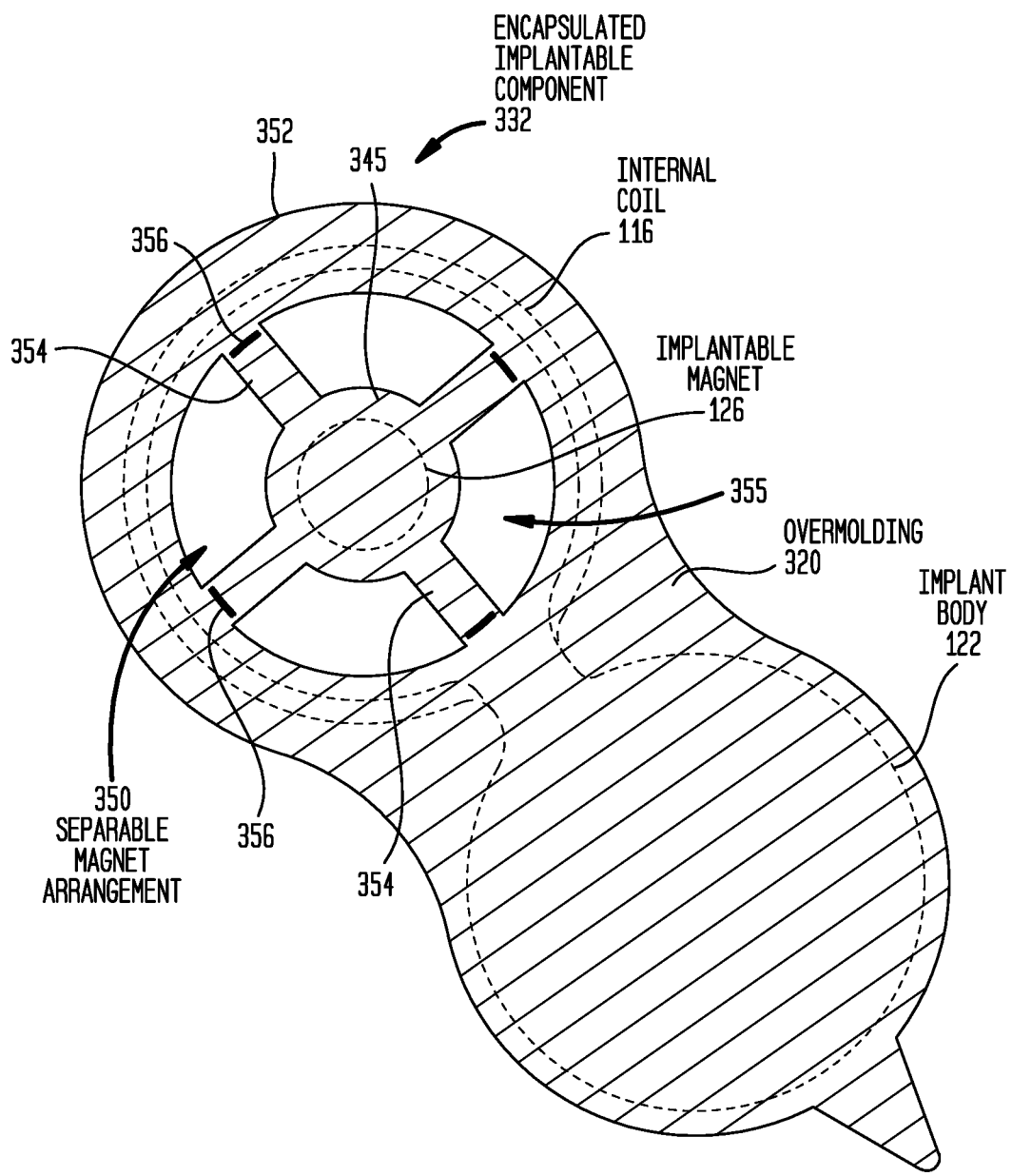

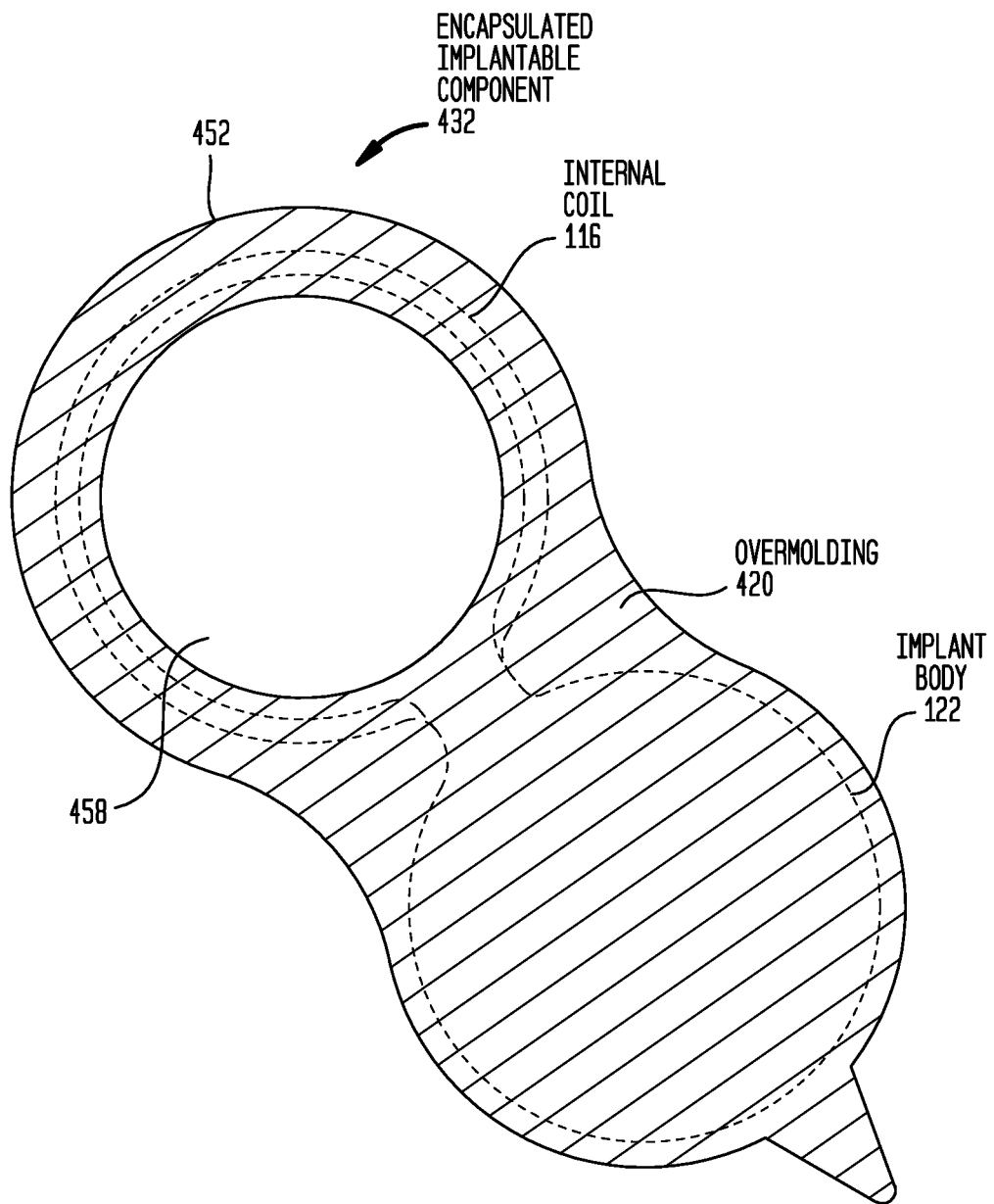

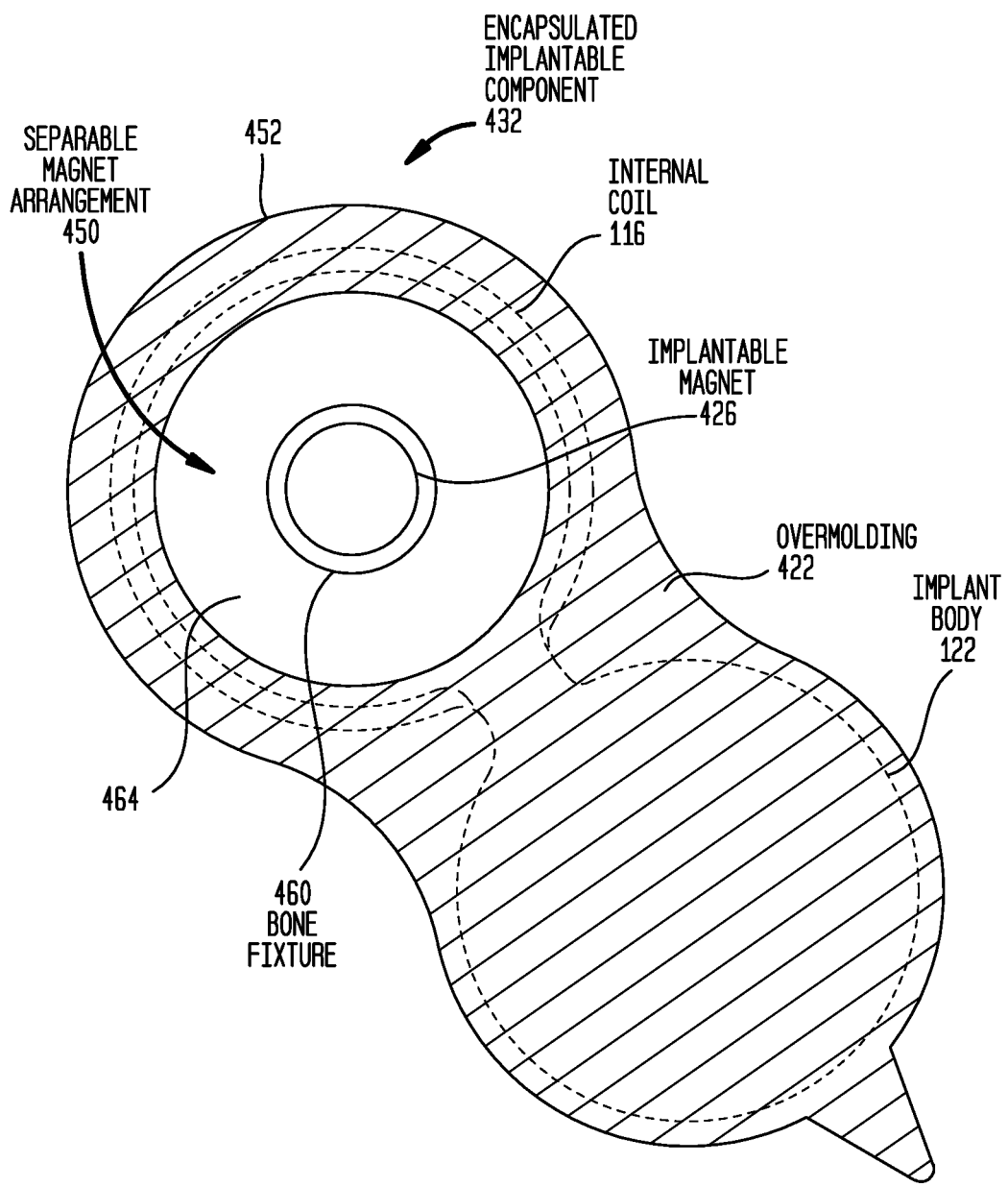

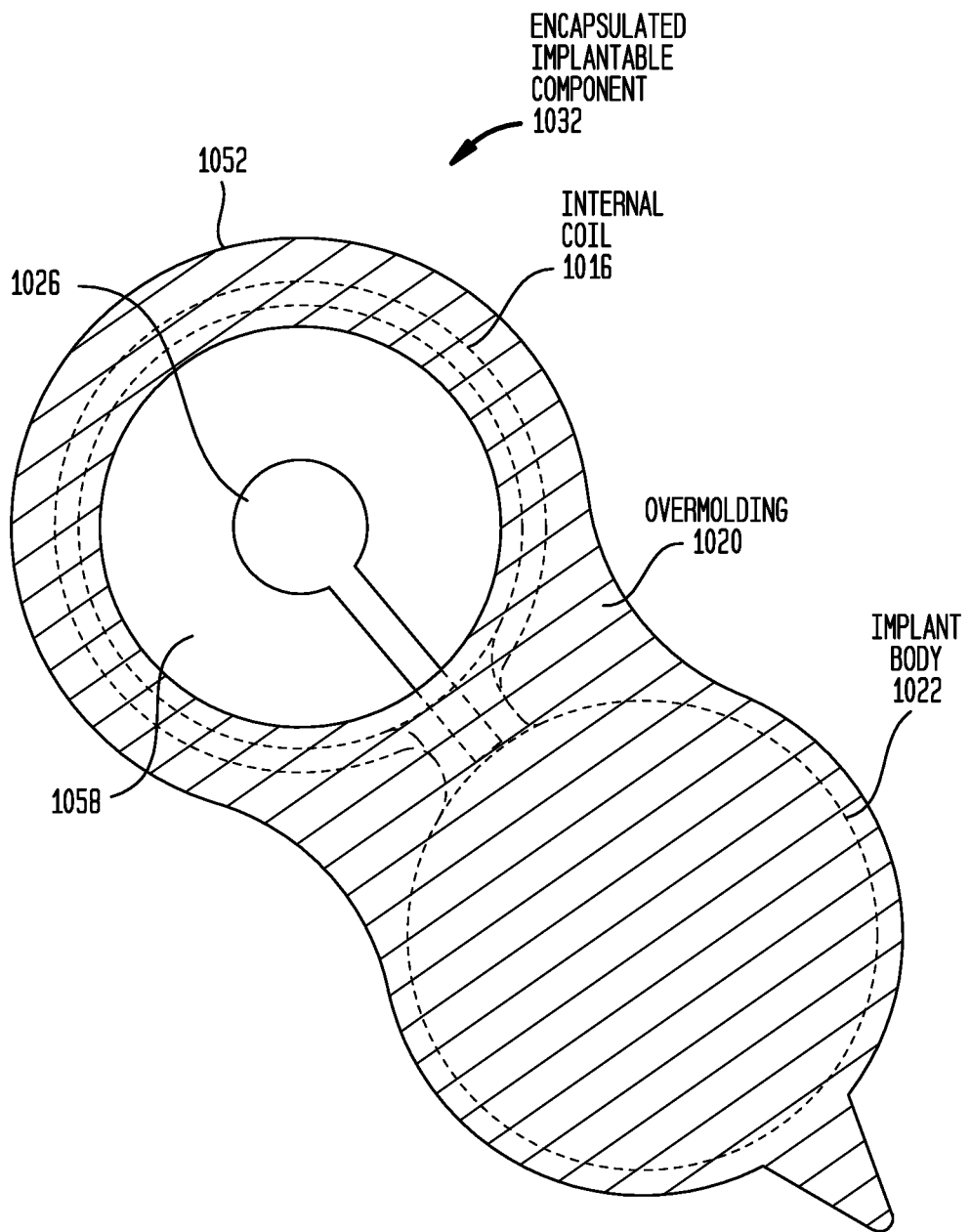

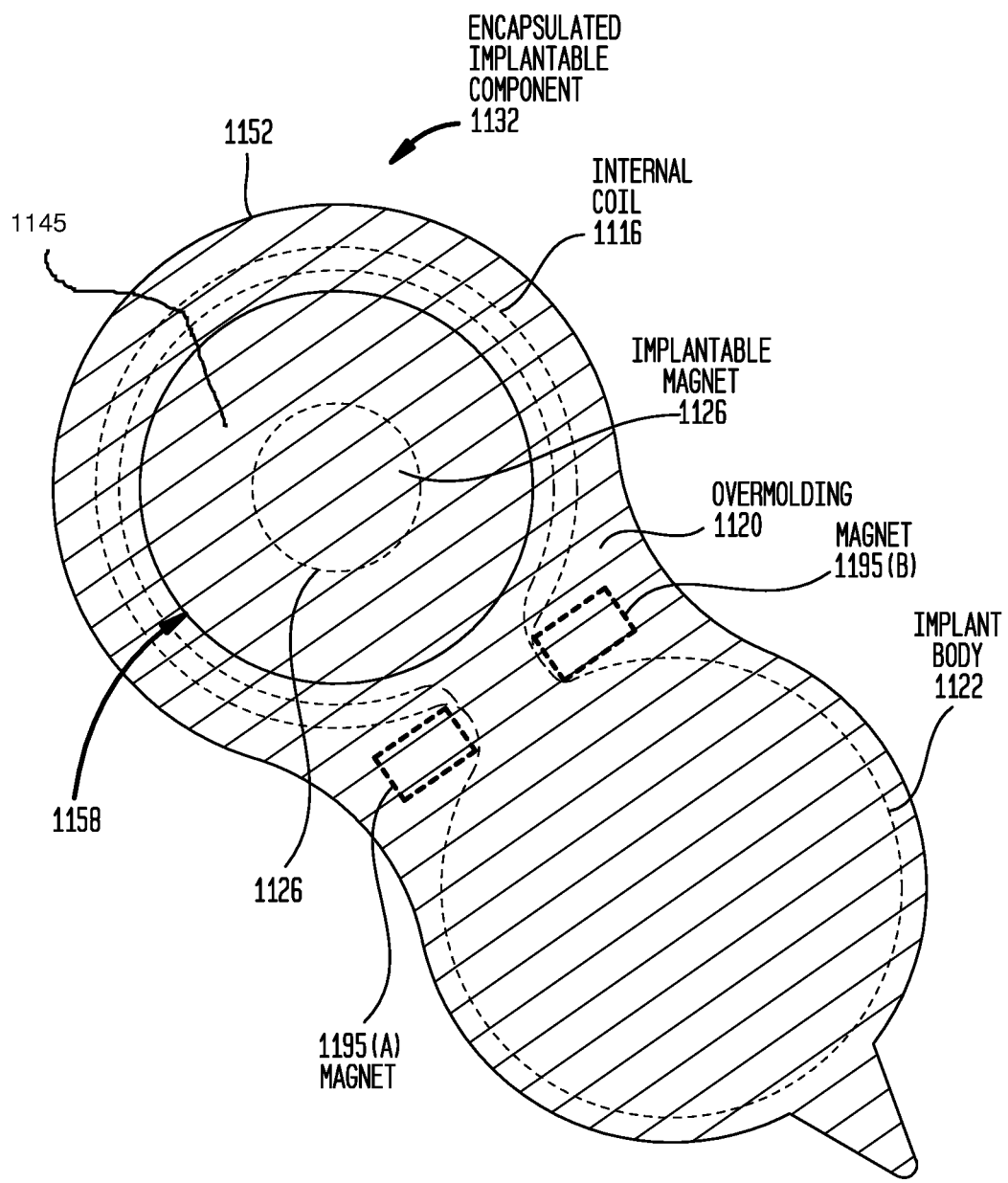

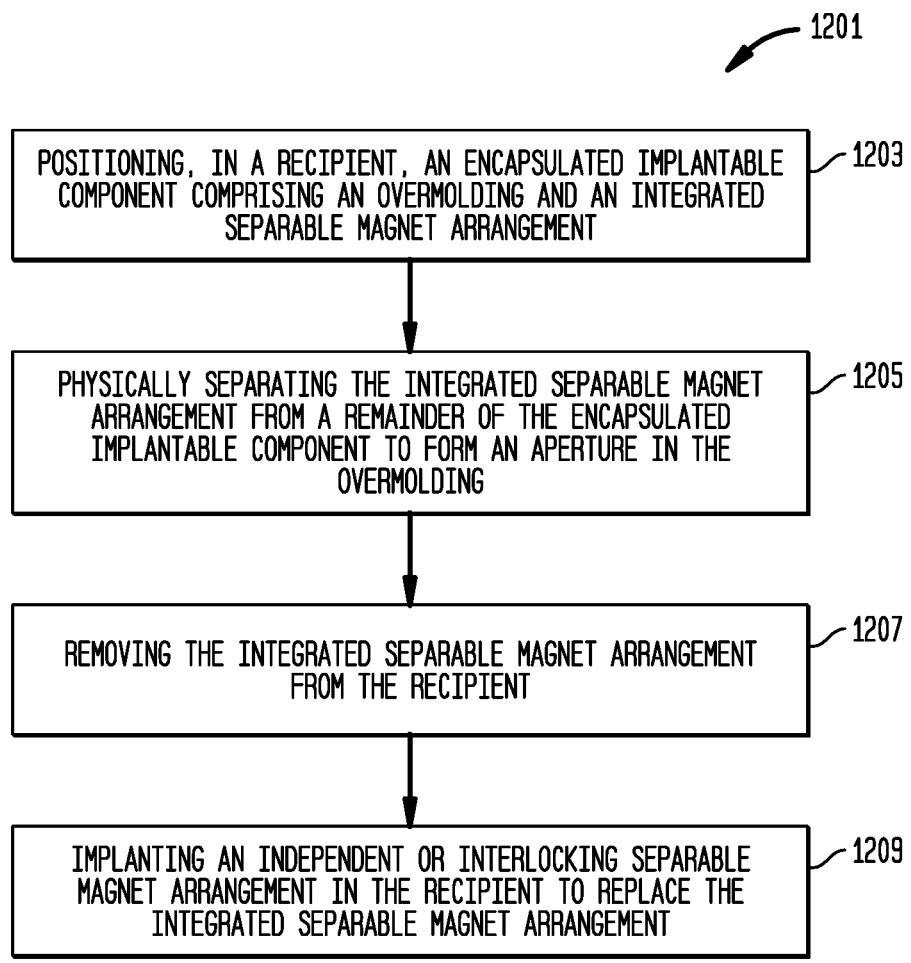

IMPLANTABLE MAGNET ARRANGEMENTS

CROSS REFERENCE TO RELATED APPLICATIONS

The present application is a continuation application of U.S. patent application Ser. No. 15/728,645, entitled "Implantable Magnet Arrangements," filed Oct. 10, 2017, which is a continuation of U.S. patent application Ser. No. 15/157,631 entitled "Implantable Magnet Arrangements," filed May 18, 2016, which claims priority to U.S. Provisional Application No. 62/206,382 entitled "Implantable Magnet Arrangements," filed Aug. 18, 2015. The content of these applications are hereby incorporated by reference herein.

BACKGROUND

Field of the Invention

The present invention relates generally to implantable medical device systems.

Related Art

Implantable medical device systems, which include one or more implantable components, have provided a wide range of therapeutic benefits to recipients over recent decades. The types of implantable medical device systems and the ranges of functions performed thereby have increased over the years. For example, many implantable medical device systems now often include one or more instruments, apparatuses, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process. Many of these functional components utilize power and/or data received from external components that are part of, or operate in conjunction with, the implantable medical device system.

SUMMARY

In one aspect, an implantable medical device is provided. The implantable medical device comprises: an implant body; an induction coil disposed adjacent to the implant body; and an implantable magnet assembly disposed within an outer perimeter of the induction coil, wherein the implantable magnet assembly is configured to be rigidly fixed to the skull bone of a recipient.

In another aspect, an implantable medical device is provided. The implantable medical device comprises: an implant body, a radio-frequency (RF) RF induction coil extending from the implant body; and an implantable magnet assembly, wherein the implantable magnet assembly includes a bone fixture, and wherein the implantable magnet assembly is configured to magnetically retain an external component of the medical device and align the external device relative to the RF induction coil.

In another aspect, a method is provided. The method comprises: positioning, in a recipient, an encapsulated implantable component comprising an overmolding and an integrated separable magnet arrangement; physically separating the integrated separable magnet arrangement from a remainder of the encapsulated implantable component to form an aperture in the overmolding; and removing the integrated separable magnet arrangement from the recipient.

BRIEF DESCRIPTION OF THE DRAWINGS

Embodiments of the present invention are described herein in conjunction with the accompanying drawings, in which:

FIG. 1 is a schematic diagram illustrating a cochlear implant system in accordance with embodiments presented herein;

FIG. 2A is a top view of an encapsulated implantable component and a separable magnet arrangement in accordance with embodiments presented herein;

FIG. 2C is a cross-sectional view of an encapsulated implantable component and a separable magnet arrangement in accordance with embodiments presented herein;

FIG. 3 is a top view of an encapsulated implantable component and a separable magnet arrangement in accordance with embodiments presented herein;

FIG. 4A is a top view of an encapsulated implantable component in accordance with embodiments presented herein;

FIG. 4B is a top view of the encapsulated implantable component of FIG. 4A and a separable magnet arrangement in accordance with embodiments presented herein;

FIG. 10A is a top view of an encapsulated implantable component and a separable magnet arrangement in accordance with embodiments presented herein;

FIG. 11 is a top view of an encapsulated implantable component and a separable magnet arrangement in accordance with embodiments presented herein; and FIG. 12 is a flowchart of a method in accordance with embodiments presented herein.

DETAILED DESCRIPTION

Figure 2B:
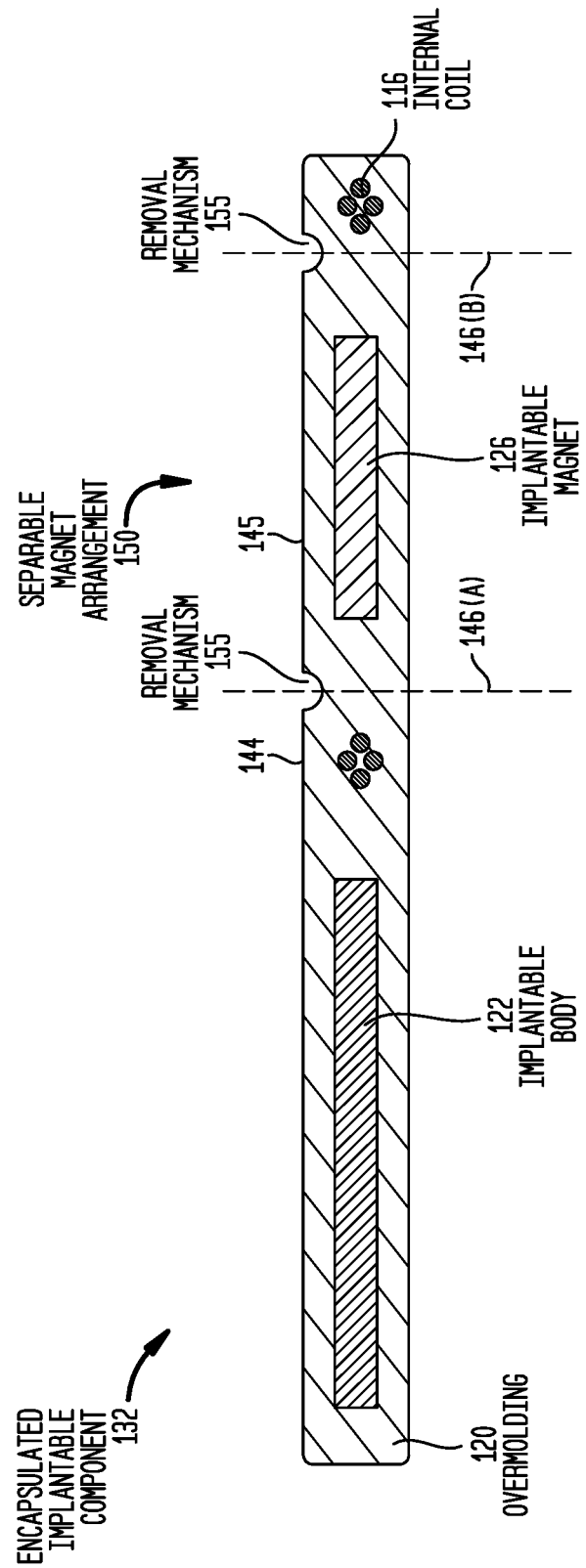
FIG. 2B is a cross-sectional view of the encapsulated implantable component and the separable magnet arrangement of FIG. 2A.

Embodiments of the present invention are generally directed to magnet arrangements for use with encapsulated implantable components. In certain embodiments, an implantable component comprises an implant body and a plurality of wire loops forming an internal coil that are encapsulated in a biocompatible overmolding. The implantable component also comprises a bone fixture positioned proximate to the plurality of wire loops and an implantable magnet attached to the bone fixture.

As described further below, certain embodiments include separable magnet arrangements comprising an implantable magnet that is fully encapsulated in, but mechanically severable from, an overmolding are sometimes referred to herein as "integrated" separable magnet arrangements (i.e., the implantable magnet is, at least initially, integrated into the overmolding). Separable magnet arrangements in which the implantable magnet is physically separate from the encapsulated implantable component are sometimes referred to herein as "independent" separable magnet arrangements.

There are different types of implantable medical device systems that include components that may be partially or fully implanted into a recipient, including bone conduction systems (e.g., percutaneous, transcutaneous, etc.), middle ear auditory prosthesis systems, direct acoustic stimulator systems, cochlear implant systems, auditory brainstem stimulator systems, implantable pacemaker systems, functional electrical stimulation systems, pain relief systems, visual prosthesis systems, etc. It is to be appreciated that embodiments presented herein may be used in connection with any of the above or other implantable medical device systems. However, merely for ease of description, embodiments of the present invention are primarily described herein with reference to a cochlear implant system.

FIG. 1 is a schematic diagram illustrating a cochlear implant system 100 in accordance with embodiments presented herein. The cochlear implant system 100 comprises an external component 102 and an implantable component 104. In this example, the implantable component 104 is a cochlear implant.

The external component 102 is directly or indirectly attached to the body of the recipient and typically comprises a sound processing unit 106 and an external coil arrangement 108. In the example of FIG. 1, the sound processing unit 106 is a behind-the-ear (BTE) unit that comprises one or more sound input elements 112 (e.g., microphones, telecoils, etc.) for receiving sound signals, a power source (not shown in FIG. 1) and a sound processor (also not shown in FIG. 1). The sound processor is configured to process electrical signals generated by the sound input element(s) 112.

The sound processing unit 106 is electrically connected to the external coil arrangement 108 via a cable or lead 110. Two portions of the external coil arrangement 108 have been removed to illustrate that an external radio frequency (RF) coil 112 and, generally, a magnet 114 fixed relative to the external coil 112, are positioned in the external coil arrangement 108.

The cochlear implant 104 comprises an implant body 122, a lead region 124, and an elongate intra-cochlear stimulating assembly 118. The implant body 122 comprises, among other components, an internal receiver/transceiver unit, sometimes referred to herein as internal transceiver unit, and a stimulator unit. The internal transceiver unit is electrically connected to an internal RF coil 116. The internal coil 116 and the implant body 122 are encapsulated in an overmolding 120 that is formed from a resiliently flexible biocompatible material (e.g., a silicone elastomer such as a polydimethylsiloxane (PDMS) polymer). The implant body 122, internal coil 116, and the flexible overmolding 120 enclosing the implant body and the internal coil are collectively and generally referred to herein as overmolded or encapsulated implantable component 132.

The external coil 112 and the internal coil 116 are typically wire antenna coils each comprising a plurality of wire loops. In order to transfer power, the external coil 112 and the internal coil 116 need to be closely-coupled. That is, the coils 112 and 116 need to be substantially aligned with one another such that a large portion of the magnetic field generated by the primary/transmitting coil passes through (i.e., is received by) the secondary/receiving coil. In the case of transmissions from the external component 102 to the cochlear implant 104, the external coil 112 is the primary coil and the internal coil 116 is the secondary coil. The alignment of the external coil 112 with the internal coil 116 is provided through a magnetic coupling between the magnet 114 in the external coil arrangement 108 and the implantable magnet 126 that is fixed relative to the internal coil 116. That is, the magnets 114 and 116 facilitate the operational alignment of the coils 112 and 116 so as to enable transcutaneous communication over a closely-coupled RF link 115.

In general, the implantable magnet 126 is a ferromagnetic or ferromagnetic element that is encased in a rigid biocompatible housing formed, for example, from titanium. For ease of illustration, the ferromagnetic or ferromagnetic element and the rigid housing are collectively and generally shown at reference 126 and are collectively referred to simply herein as an implantable magnet.

In conventional cochlear implant systems, implantable magnets are typically retained in the overmolding that encapsulates the internal coil. For example, in certain conventional arrangements, during the process in which the internal coil is overmolded in the flexible material, a small cavity (i.e., a "pocket") is formed in the overmolding and the implantable magnet is manually positioned therein.

The use of an overmolded pocket to retain the implantable magnet may be problematic in certain arrangements. For example, the small areas between the interior surfaces of the overmolded pocket and the surfaces of the implantable magnet are exposed to the implanted environment and, as such, there is a possibility that bacteria/biofilm may form around the magnet/pocket interface.

In addition, implanted magnets can negatively affect the results of Magnetic Resonance Imaging (MRI) tests by casting MRI shadows. The presence of an implanted magnet also limits the strength of the magnetic field that may be used during the MRI. As such, when a recipient needs to undergo an MRI test, an implanted magnet is typically removed by a surgeon before the recipient undergoes the MRI test. In the case of an implantable magnet located in an overmolded pocket, the surgeon opens the surgical site and manually removes the implantable magnet from the pocket. The surgeon then closes the surgical site and the recipient undergoes the MRI test. After the test, the recipient returns to the surgeon for another surgical procedure in which the implantable magnet is re-inserted into the overmolded pocket. Often, the surgeons will tear the overmolding during removal or re-insertion of the implantable magnet, particularly when using tools and small surgical incisions. The tears introduced in the overmolding create areas that are susceptible to biofilm formation and that could negatively affect the integrity of the overmolding.

As described further below, the magnet 126 is part of an independent separable magnet arrangement 150 that, in this example, is incorporated into the overmolding 120 so as to avoid the need for an overmolded pocket. That is, FIG. 1 illustrates an example in which the separable magnet arrangement 150 has a structural configuration in which the implantable magnet 126 is fully encapsulated in the overmolding 120 and, as described further below, mechanically severable therefrom. Because the implantable magnet 126 is integrated into the overmolding 120, the separable magnet arrangement 150 substantially reduces or eliminates the exposed interface between the implantable magnet 126 and the overmolding 120, while also facilitating explantation/removal of the implantable magnet from the recipient for tests, surgical upgrades, etc.

Elongate stimulating assembly 118 is configured to be at least partially implanted in the cochlea of a recipient and includes a plurality of intra-cochlear stimulating contacts 128. The stimulating contacts 128 collectively form a contact array 130 and may comprise electrical contacts and/or optical contacts. Stimulating assembly 118 extends through an opening in the cochlea (e.g., cochleostomy, the round window, etc.) and has a proximal end connected to the stimulator unit in implant body 122 via lead region 124 that extends through the recipient's mastoid bone.

As noted, FIG. 1 illustrates an example in which cochlear implant system 100 includes an external component 102 with an external sound processor. It is to be appreciated that the use of the specific external component is merely illustrative and that the techniques presented herein may be used in arrangements having an implanted sound processor, an implanted microphone, and/or an implanted power source (battery). It is also to be appreciated that the individual components referenced herein, e.g., sound input elements, the sound processor, etc., may be distributed across more than one device, e.g., two cochlear implant systems, and indeed across more than one type of device, e.g., a cochlear implant, a middle ear auditory prosthesis, a consumer electronic device, a remote control device, etc.

It is to be appreciated that the use of the external component 102, as shown in FIG. 1, is merely illustrative and that other embodiments may use alternative external components. For example, one alternative embodiment may use a so-called "button" or "coil" sound processing unit having, for example, a generally cylindrical shape. In such an embodiment, the sound input element, sound processor, external coil, and external magnet are disposed within (or adjacent to) the same housing configured to be worn at the same location as where an external coil is traditionally located. In another embodiment, one or more of the components forming part of external component 102 are implanted. However, in such an embodiment, the cochlear implant 104 operates with an external device that transcutaneously transmits power and/or data to the cochlear implant. Therefore, such embodiments still utilize an external coil that is configured to be inductively coupled to an internal coil.

FIGS. 2A and 2B are top and cross-sectional views, respectively, of the encapsulated implantable component 132 that includes the integrated separable magnet arrangement 150 in accordance with embodiments presented herein. As noted above, and as shown in FIGS. 2A and 2B, the encapsulated implantable component 132 includes an implant body 122 and an internal coil 116, both of which are encapsulated in an overmolding 120. In the embodiment of FIGS. 2A and 2B, the separable magnet arrangement 150 comprises the implantable magnet 126, a surrounding overmolding portion/region 145 that fully encapsulates the implantable magnet 126 (generally shown between lines 146(A) and 146(B) in FIG. 2B), and a removal mechanism 155. The separable magnet arrangement 150 is located at proximate to the wire loops forming the internal coil 116. For example, the separable magnet arrangement 150 may be located at the geometric center of the wire loops forming the internal coil 116, the separable magnet arrangement 150 may be located at the center of the summed magnetic field, etc.

The removal mechanism 155 is a mechanically prepared region that has sufficient strength to ensure attachment of the separable magnet arrangement 150 to the remainder of the overmolding 120, but which is also designed to facilitate surgical removal of the separable magnet arrangement 150. That is, the removal mechanism 155 is configured so as to enable a surgeon to mechanically sever or separate the separable magnet arrangement 150 from the remainder of the encapsulated component 132. In the specific arrangement of FIGS. 2A and 2B, the removal mechanism 155 is a circumferential channel or groove located at the proximal or skin-facing surface 144 of the overmolding generally between the implantable magnet 126 and the internal coil 116 (i.e., extending circumferentially around the surrounding overmolding region 145). In certain examples, the removal mechanism 155 has a configuration (e.g., circumference, shape, depth, etc.) so as to engage a surgical tool or a configuration to enable a surgeon to make an accurate cut to detach the surrounding overmolding region 145 from the rest of the overmolding 120.

FIGS. 2A and 2B illustrate one exemplary configuration for a separable magnet arrangement and associated removal mechanism forming a mechanically prepared region that facilitates surgical removal of the separable magnet arrangement 150. It is to be appreciated that removal mechanisms in accordance with embodiments presented herein may have alternative configurations.

For example, FIG. 2C is a cross-sectional view of an encapsulated implantable component 232(C) that comprises a different integrated separable magnet arrangement 250(C) in accordance with embodiments presented herein. In FIG. 2C, the implant body 122 and the internal coil 116 are each fully encapsulated in an overmolding 220(C). The separable magnet arrangement 250(C) comprises the implantable magnet 126, a surrounding overmolding portion/region 245(C) that fully encapsulates the implantable magnet 126, and a removal mechanism 255(C).

The removal mechanism 255(C) comprises two opposing circumferential channels or grooves disposed at the surfaces 244 and 247 of the overmolding 220(C) at a location that is between the implantable magnet 126 and the internal coil 116 (i.e., extending circumferentially around the surrounding overmolding region 245(C)). In particular, a first groove is located at the proximal or skin-facing surface 244 of the overmolding 220(C), while a second groove is located at the distal or skull-facing surface 247 of the overmolding. The opposing grooves forming removal mechanism 255(C) result in the surrounding overmolding region 245(C) being connected to the remainder of the overmolding 220(C) via a thinned section 249 of the overmolding. Similar to the example of FIGS. 2A and 2B, the removal mechanism 255(C) has a configuration so as to engage a surgical tool or a configuration to enable a surgeon to make an accurate cut through the thinned section 249, thereby separating the separable magnet arrangement 250(C) from the remainder of the encapsulated implantable component 232(C).

Figure 2D:
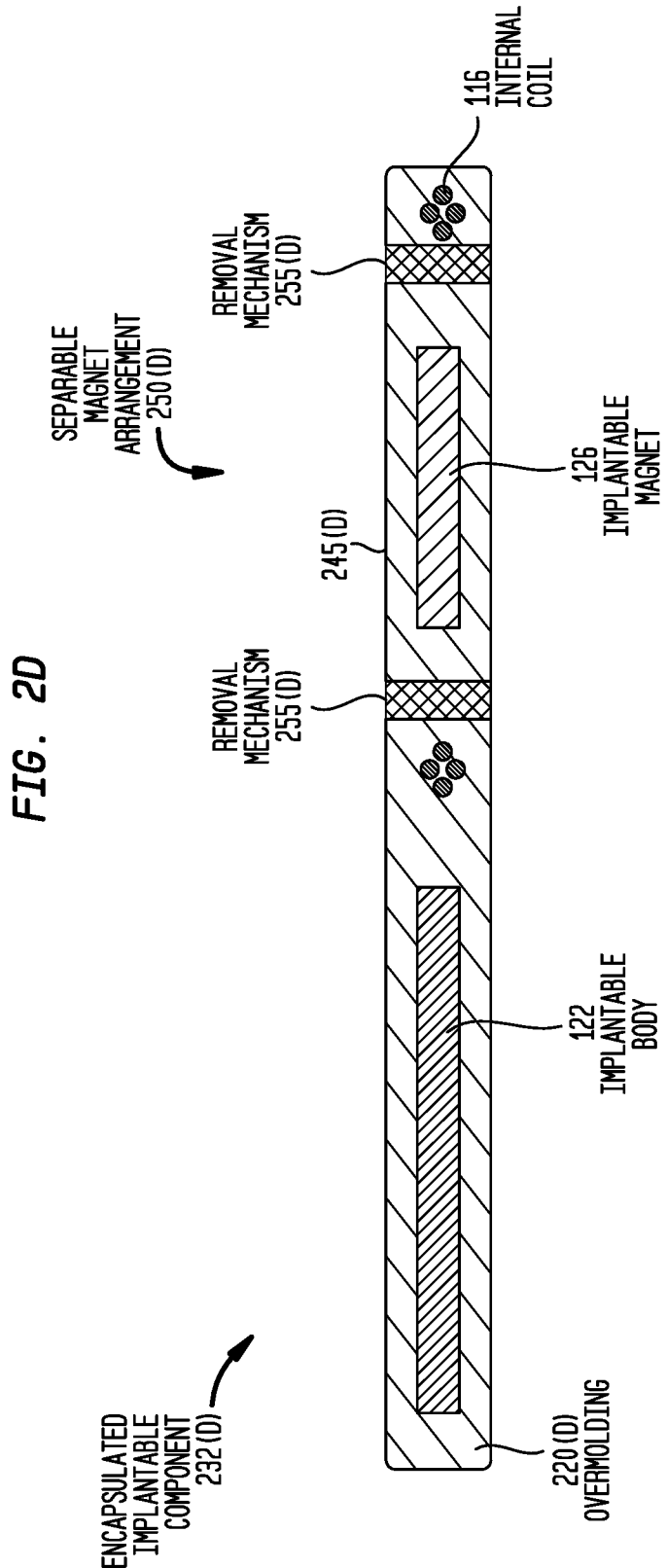
FIG. 2D is a cross-sectional view of an encapsulated implantable component and a separable magnet arrangement in accordance with embodiments presented herein.

FIG. 2D is a cross-sectional view of another encapsulated implantable component 232(D) that comprises an integrated separable magnet arrangement 250(D) in accordance with embodiments presented herein. In FIG. 2D, the implant body 122 and the internal coil 116 are each fully encapsulated in an overmolding 220(D). The separable magnet arrangement 250(D) comprises the implantable magnet 126, a surrounding overmolding portion/region 245(D) that fully encapsulates the implantable magnet 126, and a removal mechanism 255(D).

In the embodiment of FIG. 2D, the removal mechanism 255(D) comprises a circumferential region of the overmolding that is formed from a different material, or different grade of material, having mechanical properties that are different from the rest of the overmolding 220(D). More specifically, in one example, the removal mechanism 255(D) is formed from a grade or type of silicone elastomer that is substantially easier to cut (i.e., softer and/or lower tear strength) than the grade or type of silicone elastomer used for the remainder of the overmolding 220(D). In another example, the removal mechanism 255(D) is formed from a resorbable material, while the remainder of the overmolding 220(D) is formed from a non-resorbable material.

FIGS. 2B, 2C, and 2D illustrate different removal mechanisms in accordance with embodiments presented herein. It is to be appreciated that the embodiments of FIGS. 2B, 2C, and 2D are not mutually exclusive and, instead, may be combined in different forms. For example, it may be possible to use a different material, or different grade of material, (e.g., FIG. 2D) with the one or more channels or grooves (e.g., FIG. 2B or 2C).

It is also to be appreciated that the removal mechanisms shown in FIGS. 2B, 2C, and 2D are merely illustrative and other arrangements are possible. For example, rather than circumferential channels or grooves, embodiments may alternatively use channels, grooves, or other features that only extend around discrete portions of the separable magnet arrangement. Again, these discrete features could be combined with the use of a different material, or different grade of material, (e.g., FIG. 2D) so as to facilitate separation of a separable magnet arrangement from the remainder of the encapsulated implantable component.

In certain embodiments, the removal mechanisms described herein may including one or more markings (e.g., a different color, embossing, etc.) indicating the location at which a surgeon should detach the separable magnet arrangement from the remainder of the encapsulated implantable component. For example, in one specific example, a thin layer of different colored silicone (e.g., white silicone) is included in the removal mechanism to indicate where the surgeon should perform the cut.

FIG. 3 is a top view of another encapsulated implantable component 332 that comprises an integrated separable magnet arrangement 350 in accordance with embodiments of the present invention. Similar to the embodiments of FIGS. 2A-2D, the encapsulated implantable component 332 includes an implant body 122 and an internal coil 116 encapsulated in an overmolding 320. As shown, the internal coil 116 is encapsulated in an annular overmolding portion 352.

The separable magnet arrangement 350 comprises the implantable magnet 126, a surrounding overmolding portion/region 345 that fully encapsulates the implantable magnet 126, and a removal mechanism 355 formed by a plurality of discrete sections or "spokes" 354 that connect the surrounding overmolding region 345 to the annular portion 352. In operation, a surgeon can cut each of the spokes 354 so as to mechanically separate the separable magnet arrangement 350 from the remainder of the encapsulation component 332, thereby enabling the implantable magnet 126 to be removed from the recipient. As shown in FIG. 3, the spokes 354 each include an optional marking 356 indicating where the surgeon should cut the respective spoke. In certain embodiments, the markings 356 could be replaced by, or used in combination with, a mechanically prepared region as described above with references to FIGS. 2A-2D so as to further facilitate mechanical separation of separable magnet arrangement 350 from the remainder of the encapsulated implantable component 332.

As noted, the embodiments of FIGS. 2A-2D and FIG. 3 illustrate integrated separable magnet arrangements that enable a surgeon to physically separate the implantable magnet, and a portion of surrounding overmolding, from the remainder of the encapsulated implantable component. Upon removal of the respective separable magnet arrangements, the encapsulated implantable components of FIGS. 2A-2D and FIG. 3 have an arrangement that is substantially similar to that which is shown in FIG. 4A. That is, FIG. 4A is top view of an encapsulated implantable component 432 that initially had a configuration similar to, for example, that shown in one of FIGS. 2A-2D or FIG. 3, but from which the integrated separable magnet arrangement (not shown in FIG. 4A) has been removed by a surgeon.

As shown in FIG. 4A, the removal of the separable magnet arrangement results in a substantially circular aperture 458 extending through the overmolding 420 in between the wire loops forming the internal coil 116. The internal coil 116 remains encapsulated in an annular overmolding portion 452.

As noted above, it is desirable to remove implantable magnets from a recipient for a variety of reasons, including for MRI tests. However, also as noted above, presence of the implantable magnet is required to align the internal coil 116 with an external coil for transcutaneous transfer of power and/or data there between. As such, in accordance with the embodiments presented herein, an integrated separable magnet arrangement that has been removed from a recipient may be replaced by an independent separable magnet arrangement in which the implantable magnet is physically separate from the overmolding of the encapsulated implantable component.

Figure 4C:
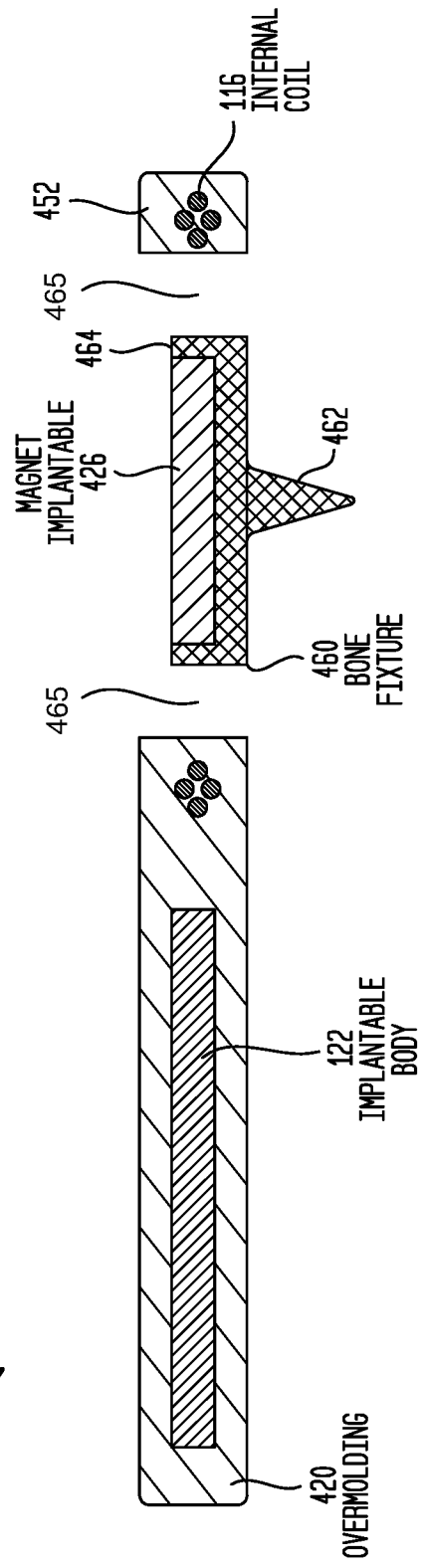
FIG. 4C is a cross-sectional view of the encapsulated implantable component and the separable magnet arrangement of FIG. 4B.

More specifically, FIGS. 4B and 4C illustrate the encapsulated implantable component 432 of FIG. 4A in combination with an independent separable magnet arrangement 450 in accordance with embodiments presented herein. In the embodiment of FIGS. 4B and 4C, the separable magnet arrangement 450 comprises an implantable magnet 426 attached to a bone fixture 460. The bone fixture 460 comprises a threaded body (shank) 462 that is configured to be inserted (e.g., screwed) into the recipient's bone generally proximate to the wire loops forming the internal coil 116. The bone fixture 460 also comprises a coupling section 464 in which the implantable magnet 426 is positioned. In this example, the implantable magnet 426 is magnetically coupled to the coupling section 464 to enable subsequent removal of the implantable magnet without removing the bone fixture 460. After insertion, a space or gap 465 remains between the separable magnet arrangement 450 and the annular overmolding portion 452.

In certain examples, the use of an alignment tool or a template could be used to facilitate the placement separable magnet arrangement 450. Proper placement of the separable magnet arrangement 450 is important to ensure alignment of the external and internal coils. In other embodiments, an adhesive, bone cement, sutures, etc. around or adjacent to the annular region 452 could also or alternatively be used to maintain the position of the coil 116 relative to the separable magnet arrangement 450.

FIGS. 4B and 4C have been described above with reference to retro-fitting an encapsulated implantable component from which another separable magnet arrangement was previously removed. However, the embodiment of FIGS. 4B and 4C should also be viewed as an example of an initial implantable arrangement for an encapsulated implantable component. That is, the encapsulated implantable component 432 may be formed during manufacturing (or in a pre-surgical procedure) to include the circular aperture 458 extending through the overmolding 420. Once the encapsulated implantable component 432 is positioned in the recipient, the surgeon could then implant the separable magnet arrangement 450 (i.e., insert the threaded body 462 into the skull) at the correct location.

The embodiments of FIGS. 4B and 4C illustrate one example in which a bone fixture is used to independently secure the separable magnet arrangement to the recipient. In alternative embodiments, a bonding agent (e.g., an ionomeric bone cement or a poly methyl methacrylate (PMMA) bone cement, a biocompatible adhesive, etc.) could be used to secure the separable magnet arrangement to the recipient. That is, the threaded body 462 could be omitted to provide a flat or textured surface that may be secured to the recipient's bone with a bonding agent.

Figure 5:
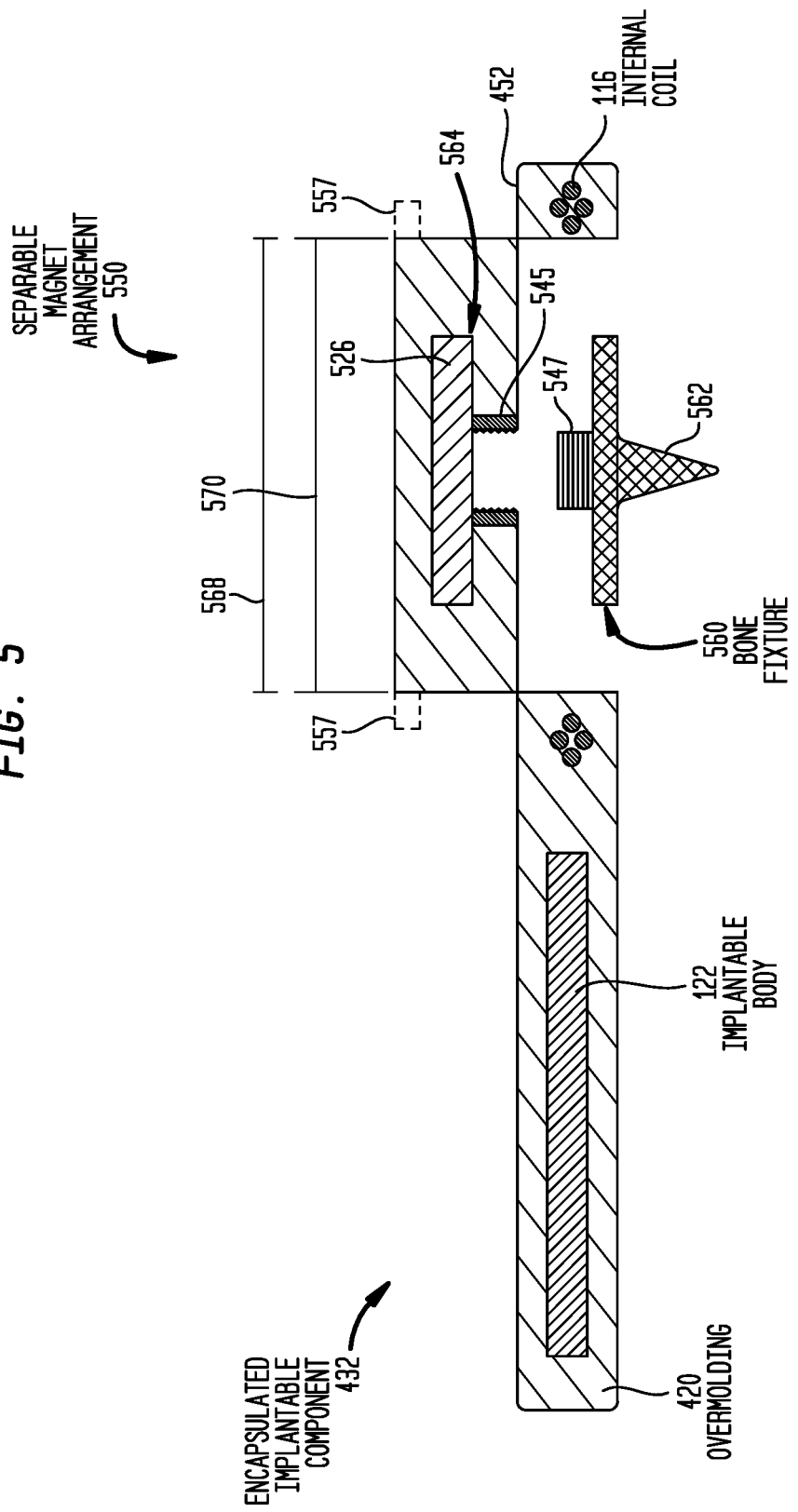
FIG. 5 is a cross-sectional view of an encapsulated implantable component and a separable magnet arrangement in accordance with embodiments presented herein.

In further embodiments, independent separable magnet arrangements may utilize different bone fixtures and/or different coupling mechanisms. For example, FIG. 5 illustrates an independent separable magnet arrangement 550 for use with the encapsulated implantable component 432 described above with reference to FIGS. 4A-4C. In this example, the independent separable magnet arrangement 550 is additionally configured for an interference fit with the encapsulated implantable component 432.

The separable magnet arrangement 550 comprises a bone fixture 560 comprising a threaded body 562 and a coupling section 564 in which an implantable magnet 526 is positioned. In this example, the coupling section 564 includes a female threaded connector 545. The female threaded connector 545 is configured to mate with a male threaded connector 547 attached to the threaded body 562.

The threaded body 562 is configured to be inserted into the recipient's bone generally proximate to the wire loops forming the internal coil 116. In this example, the implantable magnet 526 is encapsulated/overmolded in a resiliently flexible material, referred to herein as overmolding 555. The overmolding 555 is sized so as to fit tightly into the aperture 558. That is, the overmolding 555 is configured to substantially fill aperture 555 such that, after connection to the bone fixture 560, little or no space remains between the separable magnet arrangement 550 and the annular portion 452. In certain examples, the overmolding 555 has an outside dimension (e.g., width, diameter, etc.) that is larger than the outside diameter 570 of aperture 458 so as to be compressed when inserted into the aperture (i.e., an interference fit). The compression of the overmolding 555 may substantially prevent the ingress of fluid between the overmolding 555 and the annular portion 452, thereby substantially preventing the formation of biofilm there between.

As shown in FIG. 5, the separable magnet arrangement 550 may optionally include securement tabs 557. The securement tabs 557 may be formed from a substantially rigid material and are configured to exert a force in the direction of the recipient's bone.

Figure 6:
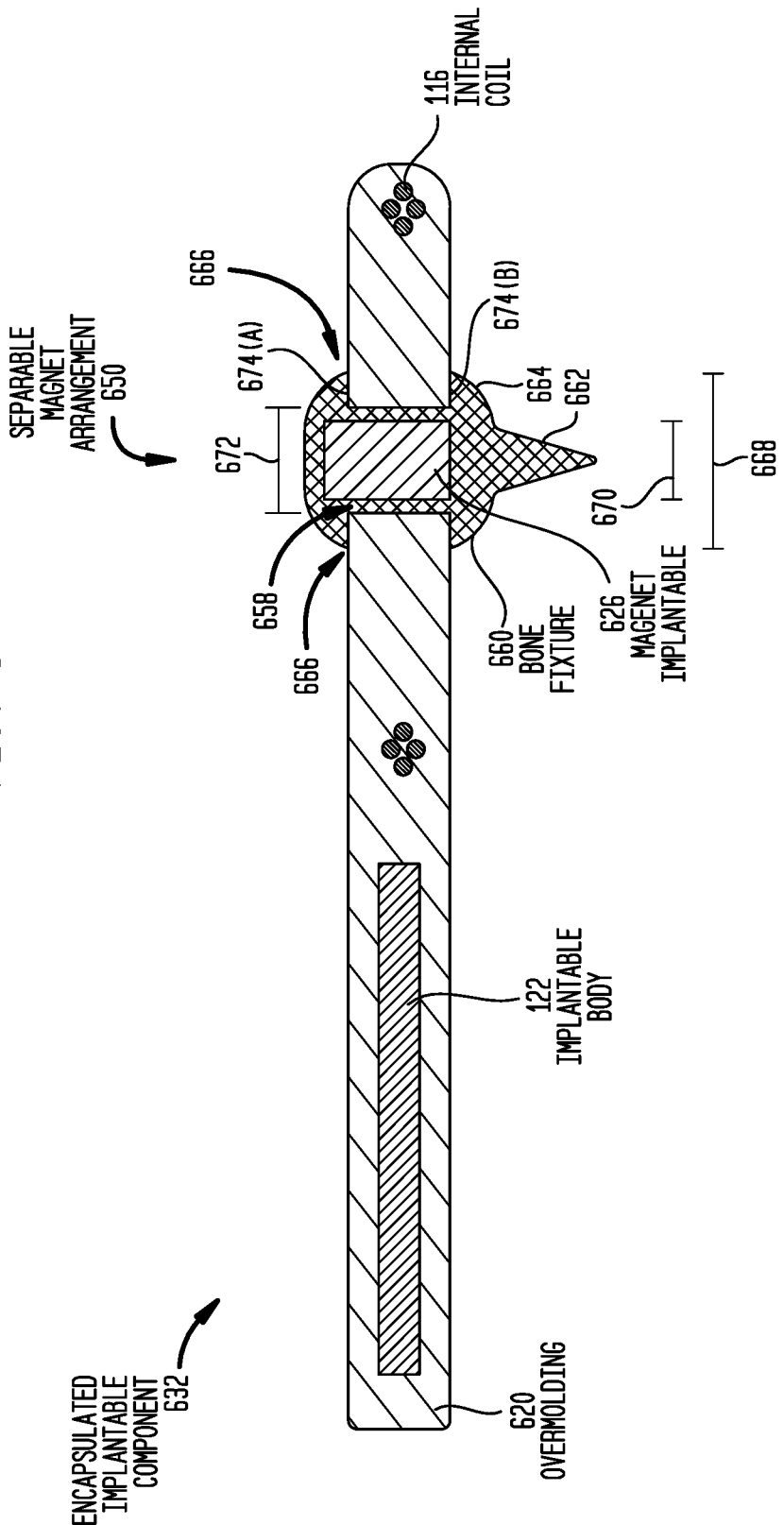
FIG. 6 is a cross-sectional view of an encapsulated implantable component and a separable magnet arrangement in accordance with embodiments presented herein.

FIG. 6 is a cross-sectional view of an embodiment of an independent separable magnet arrangement 650 that is also configured for an interference fit with an encapsulated implantable component 632. More specifically, the encapsulated implantable component 632 includes the implant body 122 and the internal coil 116, both of which are encapsulated in an overmolding 620. As shown, the encapsulated implantable component 632 includes a relatively small aperture 658 generally located proximate to the wire loops forming the internal coil 116.

The separable magnet arrangement 650 comprises an implantable magnet 626 enclosed in a bone fixture 660. The bone fixture 660 comprises a threaded body 662 that is configured to be inserted into the recipient's bone generally proximate to the wire loops forming the internal coil 116. The bone fixture 660 also comprises a coupling section 664 in which the implantable magnet 626 is positioned.

In general, the coupling section 664 has an outside dimension 668 (e.g., width, diameter, etc.) that is larger than the outside diameter 670 of aperture 658. However, the coupling section 664 also includes a circumferential channel/groove 666 with an interior dimension 672 that is approximately the same as the diameter of 670 of aperture 658.

In operation, the separable magnet arrangement 650 may be implanted into a recipient. The overmolding 620 is formed from a resiliently flexible material such that the aperture 658 may pulled over the coupling section 664 so as to be seated into the circumferential channel 666. That is, as shown in FIG. 6, the coupling section 664 is located in the aperture 658 so as to create an interference fit between the portion of the overmolding 620 surrounding the aperture and the circumferential channel 666. In this example, the overmolding 620 surrounding the aperture 658 is held between a top edge 674(A) and a bottom edge 674(B) of the circumferential channel 666.

Figure 7:
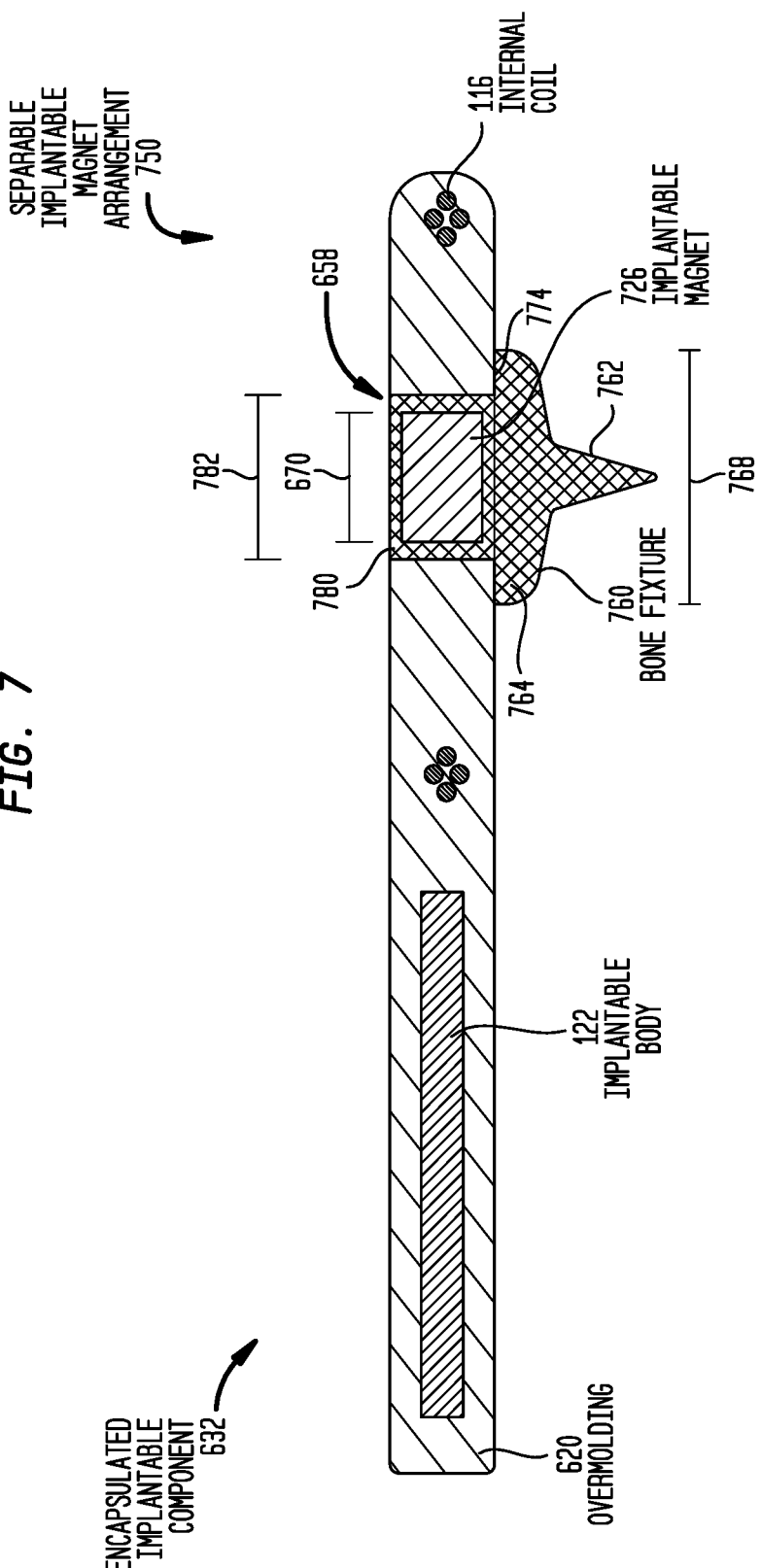
FIG. 7 is a cross-sectional view of an encapsulated implantable component and a separable magnet arrangement in accordance with embodiments presented herein.

FIG. 7 is a cross-sectional view of another independent separable magnet arrangement 750 that is configured for an interference fit with the encapsulated implantable component 632. In the embodiment of FIG. 7, the separable magnet arrangement 750 comprises an implantable magnet 726 enclosed in a bone fixture 760. The bone fixture 760 comprises a threaded body 762 that is configured to be inserted into the recipient's bone generally proximate to the wire loops forming the internal coil 116. The bone fixture 760 also comprises a coupling section 764 in which the implantable magnet 726 is positioned.

In general, the coupling section 764 has an outside dimension 768 (e.g., width, diameter, etc.) that is larger than the outside diameter 670 of aperture 658. However, the coupling section 764 also includes an upper portion 780 having an exterior dimension 782 that is smaller than the outside dimension 768. In general, the exterior dimension 782 is slightly larger than the diameter of 670 of aperture 658.

In operation, the separable magnet arrangement 750 may be implanted into a recipient. The overmolding 620 is formed from a resiliently flexible material such that the aperture 658 may pulled over the coupling section 764 so as to be seated around upper portion 782. That is, as shown in FIG. 7, the upper portion 780 of coupling section 764 is located in the aperture 658 so as to create an interference fit between the portion of the overmolding 620 surrounding the aperture and the upper portion. In this example, the overmolding 620 surrounding the aperture 658 is positioned on a ledge 774 of the coupling section 764. Additionally, since exterior dimension 782 of upper portion 780 is slightly larger than the diameter of 670 of aperture 658, the overmolding 620 is compressed and, as such, is secured around the upper portion 780.

It is to be appreciated that FIGS. 6 and 7 are merely illustrative of separable magnet arrangements configured for an interference fit/coupling with the encapsulated implantable component. It is to be appreciated separable magnet arrangements configured for an interference fit with an encapsulated implantable component in accordance with embodiments of the present invention may have other configurations.

Figure 8:
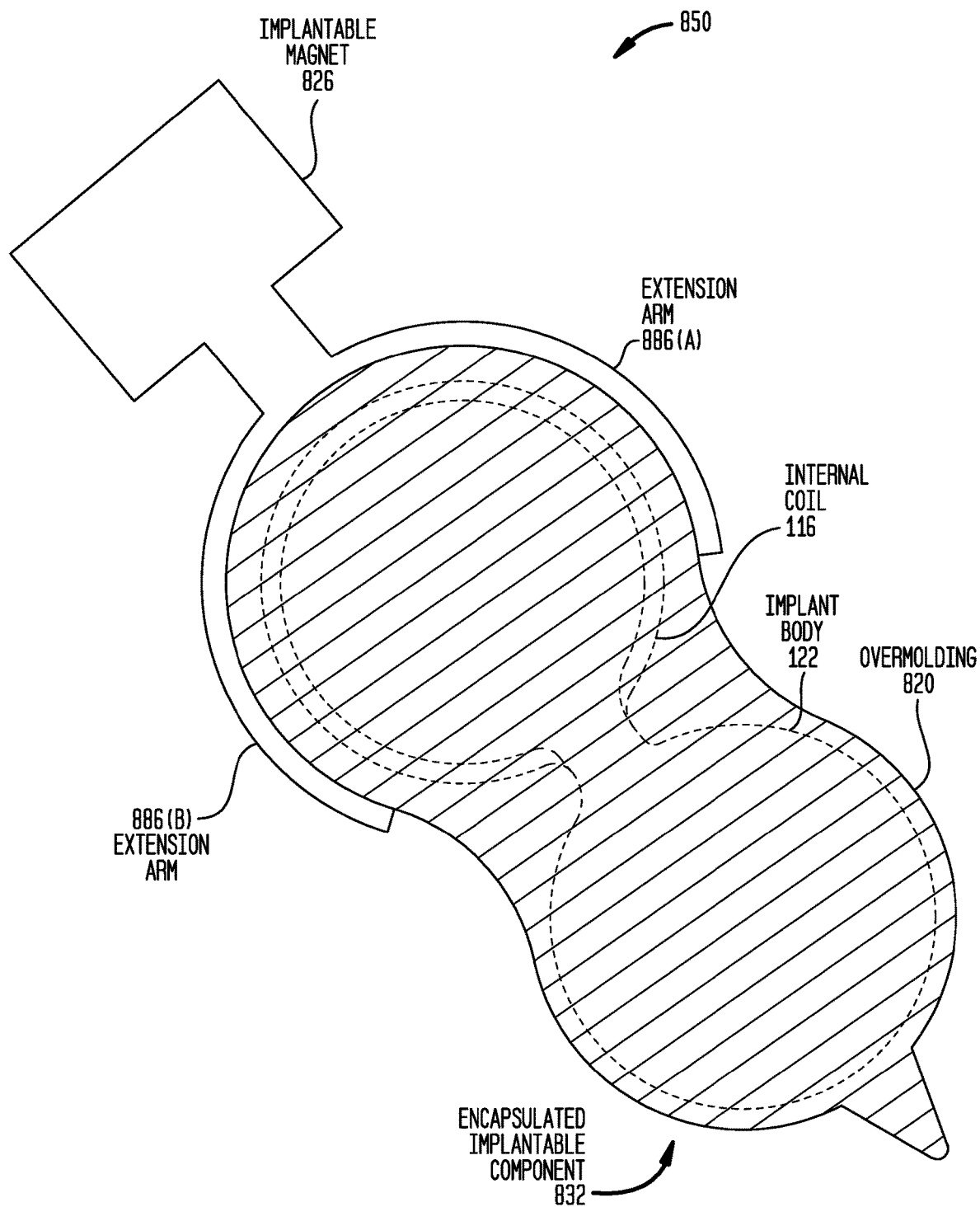
FIG. 8 is a top view of an encapsulated implantable component and a separable magnet arrangement in accordance with embodiments presented herein.

FIG. 8 is a schematic diagram illustrating an "interlocking" separable magnet arrangement 850. As used herein, an interlocking separable magnet arrangement is a separable magnet arrangement having a structural configuration to enable mechanical interlocking with an encapsulated implantable component 832. In this example, the encapsulated implantable component 832 includes the implant body 122 and the internal coil 116 encapsulated in an overmolding 820. However, unlike encapsulated implantable component 432 (FIG. 4A), the encapsulated implantable component 832 does not include an aperture extending through the overmolding 820.

The separable magnet arrangement 850 comprises an implantable magnet 826 and two extension arms 886(A) and 886(B) extending from the implantable magnet. As shown in FIG. 8, the extension arms 886(A) and 886(B) are configured to fit around and mechanically engage the outer edge of the portion of the overmolding 820 in which internal coil 116 is positioned. The mechanical engagement between the extension arms 886(A) and 886(B) and the outer surface of the overmolding 820 functions to retain the separable magnet arrangement 850 in a desired location.

In certain examples, the extension arms 886(A) and 886(B) are formed from a rigid material (e.g., titanium, platinum, etc.) having a thickness that makes the extension arms 886(A) and 886(B) pliable. In other embodiments, the extension arms 886(A) and 886(B) are formed from an elastomer material having sufficient rigidity to engage the overmolding 820.

It is to be appreciated that the separable magnet arrangement 850 may be partially or fully enclosed in its own encapsulation/molding, depending on what material is used form the extension arms. However, merely for ease of illustration, the separable magnet arrangement 850 has been shown in FIG. 8 without an encapsulation enclosing the implantable magnet 826 and/or the extension arms 886(A) and 886(B).

Figure 9:
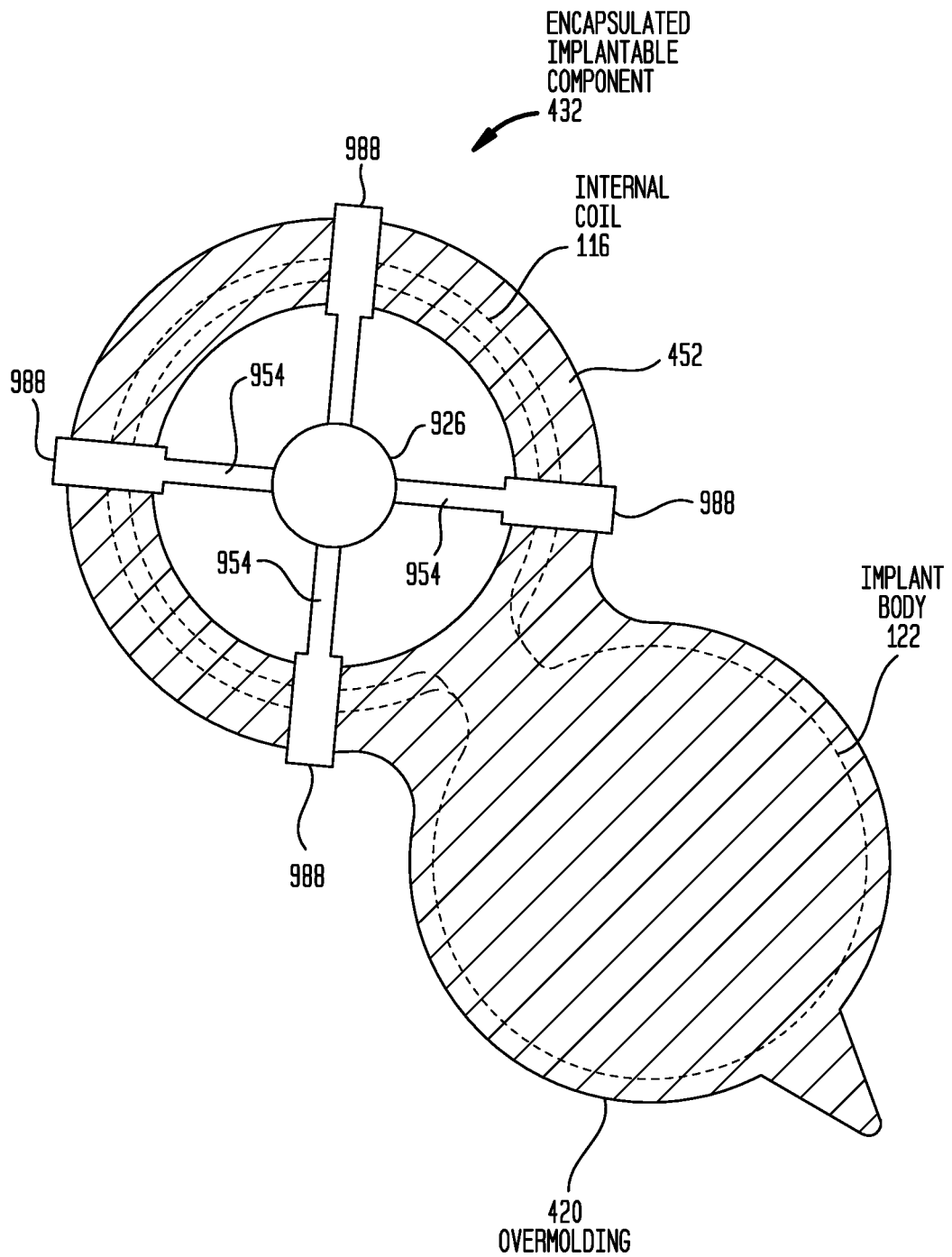
FIG. 9 is a top view of an encapsulated implantable component and a separable magnet arrangement in accordance with embodiments presented herein.

FIG. 9 is a schematic diagram illustrating another interlocking separable magnet arrangement 950 that is configured for mechanical interlocking with the encapsulated implantable component 432 shown in FIG. 4A. In this example, the separable magnet arrangement 950 comprises an implantable magnet 926 configured to be located proximate to the wire loops forming the internal coil 116. The separable magnet arrangement 950 comprises a plurality of discrete sections or "spokes" 954 that extend from the implantable magnet 926. The spokes 954 each terminate in a connector 988 that is configured to mechanically engage the annular portion 452 that encapsulates the internal coil 116. In one example, the spokes 954 and connectors 988 are formed from, for example, a silicone elastomer and the connectors are fit in place by pressing and elastically deforming the connectors and/or annular portion 452. In other embodiments, the spokes 954 and connectors 988 are formed from a rigid material (e.g., titanium, platinum, etc.).

It is to be appreciated that the separable magnet arrangement 950 may be partially enclosed in its own encapsulation/molding. However, merely for ease of illustration, the separable magnet arrangement 950 has been shown in FIG. 9 without an encapsulation/molding enclosing the implantable magnet 926, spokes 954 and/or connectors 988.

Figure 10B:
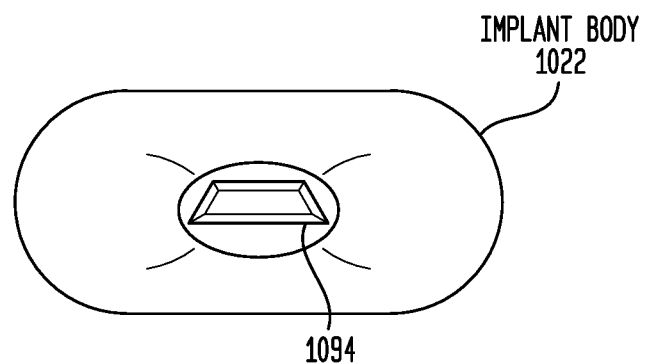
FIG. 10B is a side view of a receptacle formed in an implant body in accordance with the embodiment of FIG. 10A.
Figure 10C:
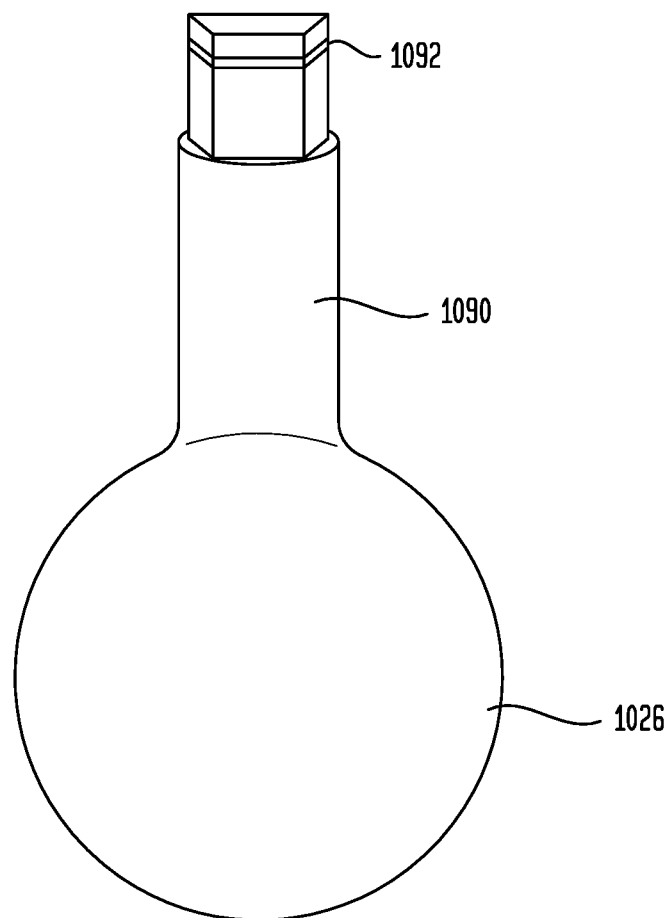
FIG. 10C is a perspective view of the separable magnet arrangement of FIG. 10A.

FIGS. 10A-10C are schematic diagrams illustrating another interlocking separable magnet arrangement 1050 that is configured for mechanical interlocking with an encapsulated implantable component 1032. In this example, the encapsulated implantable component 1032 includes an implant body 1022 and an internal coil 1016, both of which are encapsulated in an overmolding 1020. The overmolding 1020 includes a substantially circular aperture 1058 extending through the overmolding. The internal coil 1016 remains encapsulated in an annular overmolding portion 1052.

The separable magnet arrangement 1050 comprises an implantable magnet 1026 configured to be located proximate to the wire loops forming the internal coil 1016. The separable magnet arrangement 1050 also comprises a substantially rigid connector arm 1092 extending from the implantable magnet 1026. As shown in FIGS. 10B and 10C, the connector arm 1092 terminates in a plug 1092 that is configured to mechanically mate with a receptacle/socket 1094 disposed in implant body 1022. The plug 1092 and socket 1094 may each be asymmetrical to ensure that the plug can only inserted into the socket with a specified orientation. Additionally, the plug 1092 and socket 1094 may provide a snap-in interface (e.g., the plug and/or socket may be elastically deformable to facilitate a tight fit therebetween).

The embodiment shown in FIGS. 10A-10C may be interesting from a pre-MRI surgery point of view since a small incision would be enough (i.e., about as wide as the implantable magnet) to remove the magnet and later replace it. At extraction and/or re-insertion, the void in the tissue could receive an injection of antibiotics to avoid bacterial colonization. Furthermore, since the implantable magnet 1026 is rigidly connected to the implant body 1022, the magnet would be stabilized during MRI (i.e., it can't turn that much since the implant body helps to keep it in place).

FIG. 11 illustrates another separable magnet arrangement 1150 that is configured to be magnetically coupled to an encapsulated implantable component 1132. In this example, the encapsulated implantable component 1132 includes an implant body 1122 and an internal coil 1116, both of which are encapsulated in an overmolding 1120. The overmolding 1120 includes a substantially circular aperture 1158 extending through the overmolding. The internal coil 1116 remains encapsulated in an annular overmolding portion 1152.

In the embodiment of FIG. 11, the separable magnet arrangement 1150 comprises an implantable magnet 1126, a surrounding overmolding portion/region 1145 that fully encapsulates the implantable magnet 1126. The surrounding overmolding region 1145 has a configuration so as to be positioned in, and to substantially fill, the aperture 1158.

The encapsulated implantable component 1132 further comprises magnets 1195(A) and 1195(B) generally on the implant body 1122 adjacent to the internal coil 1116. The magnets 1195(A) and 1195(B) are configured to magnetically couple to the implantable magnet 1126 when the separable magnet arrangement 1150 is positioned in the aperture 1158. That is, FIG. 11 illustrates a magnetic coupling arrangement for securement of the separable magnet arrangement 1150 adjacent to the encapsulated implantable component 1132.

In certain embodiments, an implant body (as described above) may include a feature that facilitates proper collocating of the implant and a separable magnet arrangement. For example, the implant body may include a horizontal pedestal that is placed in a channel that has been predrilled into the bone The pedestal provides a feature from which a surgeon can reliably assess using, for example a surgical template, where the drilling for a bone screw (included in a separable magnet arrangement) needs to occur.

As noted above, embodiments of the present invention generally enable surgical removal of a separable magnet arrangement, which includes an implantable magnet, without removal of an encapsulated implantable component that relies upon the implantable magnet for operation. FIG. 12 is a flowchart of one example surgical method 1201 utilizing separable magnet arrangements in accordance with embodiments presented herein.

Method 1201 begins at 1203 wherein an encapsulated implantable component comprising an overmolding and an integrated separable magnet arrangement is positioned in a recipient. At 1205, the integrated separable magnet arrangement is physically separated from a remainder of the encapsulated implantable component to form an aperture in the overmolding. At 1207, the integrated separable magnet arrangement from the recipient.

As noted above, it is desirable to remove implantable magnets from a recipient for a variety of reasons, including for MRI tests. However, also as noted above, presence of the implantable magnet is required for alignment of external and internal coils for transcutaneous transfer of power and/or data there between. As such, in accordance with the embodiments presented herein, at 1209, method 1201 includes replacement of the integrated separable magnet arrangement that has been removed from a recipient with an independent or interlocking separable magnet arrangement.

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of electrically-stimulating auditory prosthesis that might also be proposed when a recipient experiences sensorineural hearing loss due to damage to the auditory nerve.

Bone conduction recipients may initially be fitted with a transcutaneous bone conduction device (i.e., a device that uses an implanted magnetic bone fixture for transcutaneous transmission of vibrations from an external transducer/vibrator). However, in certain cases, the hearing capability of bone conduction recipients may deteriorate such that they no longer receive suitable benefit from the bone conduction device (i.e., increased sensorineural hearing loss). As a result, these recipients are candidates for upgrades to, for example, a cochlear implant. The embodiments presented herein facilitate such upgrades from bone conduction devices to cochlear implants.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device, comprising:
   an implant body;
   an induction coil extending from the implant body;
   a biocompatible overmolding encapsulating the implant body and the induction coil, wherein the biocompatible overmolding defines an aperture within an area bounded by the induction coil, and wherein the aperture comprises a first end having a first diameter and a second end having a second diameter; and
   an implantable magnet assembly comprising an implantable magnet, wherein at least a portion of the implantable magnet assembly is configured to be positioned in the aperture, and the at least a portion of the implantable magnet assembly positioned in the aperture and extending from the first end of the aperture to the second end of the aperture comprises a greater diameter than the first diameter and the second diameter of the aperture to provide an interference fit with the aperture.

2. The implantable medical device of claim 1, wherein the implantable magnet assembly comprises:
   a bone fixture in which the implantable magnet is disposed, wherein the bone fixture comprises a threaded body configured to be screwed into a recipient's bone; and
   a coupling section attached to the threaded body, wherein the coupling section comprises the at least a portion of the implantable magnet assembly configured to be positioned in the aperture.

3. The implantable medical device of claim 1, wherein the at least a portion of the implantable magnet assembly is configured to compress a portion of the biocompatible overmolding surrounding the aperture.

4. The implantable medical device of claim 1, wherein the at least a portion of the implantable magnet assembly includes a circumferential channel formed into a coupling section of the implantable magnet assembly to provide a first edge and a second edge of the coupling section, and wherein the first edge and the second edge extend radially outward from the circumferential channel.

5. The implantable medical device of claim 4, wherein the first edge and the second edge of the coupling section are configured to capture opposite sides of the biocompatible overmolding to position the at least a portion of the implantable magnet assembly within the aperture.

6. The implantable medical device of claim 1, wherein the implantable magnet assembly includes:
   a first portion having an outside dimension that is larger than a diameter of the aperture; and
   a second portion configured to be positioned in the aperture, wherein the second portion has an exterior dimension that is smaller than the outside dimension and wherein the exterior dimension is larger than the diameter of the aperture such that, when positioned in the aperture, the second portion is configured to compress a portion of the biocompatible overmolding surrounding the aperture.

7. The implantable medical device of claim 6, wherein the biocompatible overmolding is formed from a resiliently flexible material such that the aperture is configured to be pulled over the second portion and seated on a ledge created by the first portion of the implantable magnet assembly.

8. The implantable medical device of claim 1, wherein the implantable magnet is configured to magnetically retain an external device and align the external device relative to the induction coil.

9. The implantable medical device of claim 1, wherein the implantable magnet assembly is aligned concentrically with the induction coil.

10. An implantable medical device, comprising:
an implant body;
an induction coil disposed adjacent to the implant body and electrically connected to one or more components within the implant body;
a resiliently flexible encapsulation disposed around the implant body and the induction coil, wherein the resiliently flexible encapsulation includes an aperture that is concentric with the induction coil, and wherein the aperture comprises a first end having a first diameter and a second end having a second diameter; and
a bone fixture comprising a portion configured to be positioned in the aperture for rigid fixation to a bone of a recipient, wherein the portion of the bone fixture comprises a third diameter that is greater than the first diameter and the second diameter of the aperture to flexibly mate with a portion of the resiliently flexible encapsulation defining the aperture.

11. The implantable medical device of claim 10, wherein the bone fixture comprises:
a threaded body configured to be screwed into a recipient's bone; and
a coupling section attached to the threaded body, wherein the coupling section comprises the portion of the bone fixture configured to be positioned in the aperture.

12. The implantable medical device of claim 11, wherein the coupling section is configured to compress the portion of the resiliently flexible encapsulation defining the aperture.

13. The implantable medical device of claim 11, wherein the portion of the bone fixture includes a circumferential channel formed into the coupling section to provide a first edge and a second edge of the coupling section, and wherein the first edge and the second edge extend radially outward from the circumferential channel.

14. The implantable medical device of claim 13, wherein the first edge and the second edge of the coupling section are configured to capture opposite sides of the resiliently flexible encapsulation to position the portion of the bone fixture within.

15. The implantable medical device of claim 11, wherein the coupling section includes:
a first portion having an outside dimension that is larger than a diameter of the aperture; and
a second portion configured to be positioned in the aperture, wherein the second portion has an exterior dimension that is smaller than the outside dimension and wherein the exterior dimension is larger than the diameter of the aperture such that, when positioned in the aperture, the second portion is configured to compress the portion of the resiliently flexible encapsulation defining the aperture.

16. The implantable medical device of claim 15, wherein the resiliently flexible encapsulation is configured such that the aperture is configured to be pulled over the second portion and seated on a ledge created by the first portion of the coupling section.

17. The implantable medical device of claim 10, wherein the bone fixture includes a magnet configured to magnetically retain an external device and align the external device relative to the induction coil.

18. The implantable medical device of claim 10, wherein the implant body comprises a hermetic enclosure, and the induction coil comprises at least one wire loop disposed outside the hermetic enclosure.

19. A method, comprising:
positioning an implant body and an induction coil extending from the implant body in the body of a recipient, wherein the implant body and induction coil are encapsulated in a biocompatible overmolding, and wherein the biocompatible overmolding defines an aperture within an area bounded by the induction coil; and
positioning a bone fixture in the aperture, wherein the bone fixture comprises a coupling section, the coupling section includes a circumferential channel with an interior dimension that is at least one of approximately the same size as or larger than a diameter of the aperture, and wherein the circumferential channel is configured to mate with a portion of the biocompatible overmolding defining the aperture.

20. The method of claim 19, wherein the bone fixture comprises a threaded body attached to the coupling section, and wherein the method further comprises:
screwing the threaded body into a bone of the recipient.

21. An implantable medical device, comprising:
an implant body;
an induction coil extending from the implant body;
a biocompatible overmolding encapsulating the implant body and the induction coil, wherein the biocompatible overmolding defines an aperture within an area bounded by the induction coil, and wherein the aperture comprises a first end having a first diameter and a second end having a second diameter; and
an implantable magnet assembly comprising:
an implantable magnet, wherein at least a portion of the implantable magnet assembly is configured to be positioned in the aperture, and the at least a portion of the implantable magnet assembly comprises a third diameter that is greater than the first diameter and the second diameter of the aperture to provide an interference fit with the aperture,
a bone fixture in which the implantable magnet is disposed, wherein the bone fixture comprises a threaded body configured to be screwed into a recipient's bone; and
a coupling section attached to the threaded body, wherein the coupling section comprises the at least a portion of the implantable magnet assembly configured to be positioned in the aperture.

22. An implantable medical device, comprising:
an implant body;
an induction coil extending from the implant body;
a biocompatible overmolding encapsulating the implant body and the induction coil, wherein the biocompatible overmolding defines an aperture within an area bounded by the induction coil, and wherein the aperture comprises a first end having a first diameter and a second end having a second diameter; and an implantable magnet assembly comprising an implantable magnet, wherein at least a portion of the implantable magnet assembly is configured to be positioned in the aperture, and the at least a portion of the implantable magnet assembly comprises a third diameter that is greater than the first diameter and the second diameter of the aperture to provide an interference fit with the aperture, wherein the at least a portion of the implantable magnet assembly includes a circumferential channel formed into a coupling section of the implantable magnet assembly to provide a first edge and a second edge of the coupling section, and wherein the first edge and the second edge extend radially outward from the circumferential channel, wherein the first edge and the second edge of the coupling section are configured to capture opposite sides of the biocompatible overmolding to position the at least a portion of the implantable magnet assembly within the aperture.

\* \* \* \* \*